US008361759B2

(12) United States Patent
Yeboah et al.

(10) Patent No.: US 8,361,759 B2
(45) Date of Patent: Jan. 29, 2013

(54) PROCESS FOR PRODUCING FARNESYLATED DIBENZODIAZEPINONE BY FERMENTATION

(75) Inventors: Faustinus Yeboah, Longueuil (CA); Mahmood Piraee, Cambridge (GB)

(73) Assignee: Thallion Pharmaceuticals Inc., Montreal, Quebec (CA)

( * ) Notice: Subject to any disclaimer, the term of this patent is extended or adjusted under 35 U.S.C. 154(b) by 30 days.

(21) Appl. No.: 12/764,537

(22) Filed: Apr. 21, 2010

(65) Prior Publication Data

US 2010/0204468 A1   Aug. 12, 2010

Related U.S. Application Data

(63) Continuation of application No. 11/785,226, filed on Apr. 16, 2007, now abandoned.

(60) Provisional application No. 60/791,903, filed on Apr. 14, 2006.

(51) Int. Cl.
*C12P 17/10* (2006.01)

(52) U.S. Cl. ............... 435/121; 435/170; 435/252.1; 540/495

(58) Field of Classification Search .......... 435/121, 435/170, 252.1; 540/495
See application file for complete search history.

(56) References Cited

U.S. PATENT DOCUMENTS

| | | | |
|---|---|---|---|
| 5,188,952 A | 2/1993 | Carver | |
| 5,541,181 A | 7/1996 | Ohkuma et al. | |
| 6,733,998 B1 | 5/2004 | Thorson | |
| 7,101,872 B2 * | 9/2006 | Bachmann et al. | 514/220 |
| 7,186,713 B2 | 3/2007 | Farnet | |
| 2005/0043297 A1 | 2/2005 | Bachmann et al. | |
| 2009/0186878 A1 * | 7/2009 | Morris et al. | 514/220 |

FOREIGN PATENT DOCUMENTS

| | | |
|---|---|---|
| CA | 2538147 | 8/2004 |
| WO | 2007/089657 | 8/2007 |
| WO | 2007/118320 | 10/2007 |

OTHER PUBLICATIONS

Charan, R.D. et al, Diazepinomicin, A New Antimicrobial Alkaloid From A Marine *Micromonospora* sp. 2004, Journal of Natural Products, vol. 67, No. 8, pp. 1431-1433.
Slide Presentation given at the Society of Industrial Microbiology, "Microbes Produce Novel Structures—The Origins and Development of ECO-4601/Diazepinomicin," 21 slides, Chicago, Illinois, Aug. 21-25, 2005, McAlpine et al.
International Search Report from PCT/CA2007/00629, dated Jul. 25, 2007.
International Search Report from PCT/US07/02291, dated Nov. 7, 2007.
Ahuja et al, Application of Plackett-Burman Design and Response Surface Methodology to Achieve Exponential Growth for Aggregated Shipworm Bacterium, Biotechnology and Bioengineering, vol. 85, No. 6, Mar. 20, 2004, pp. 666-675.
Balaraman et al, Optimization of Media Composition for the Production of Cyclosporin A by Tolypocladium Species, Indian J. Med. Res. 123, Apr. 2006, pp. 525-530.
Carnes, Fermentation Design for the Manufacture of Therapeutic Plasmid DNA, BioProcess International, Oct. 2005, pp. 2-7.
Ichiba et al, Analysis of Urinary Metabolites of Polycyclic Aromatic Hydrocarbons in Incineration Workers, Journal of Occupational Health, vol. 49, 2007, pp. 159-164.
Lynd et al, Microbial Cellulose Utilization: Fundamentals and Biotechnology, Microbiology and Molecular Biology Reviews, vol. 66, No. 3, Sep. 2002, pp. 506-577.
Rosi et al, Mutational Biosynthesis by Idiotrophs of *Micromonospora purpurea*, The Journal of Antibiotics, Jan. 1977, vol. 30, No. 1, pp. 88-97.
Shoun et al, Denitrification by Actinomycetes and Purification of Dissimilatory Nitrite Reductase and Azurin from *Streptomyces thioluteus*, Journal of Bacteriology, vol. 180, No. 17, Sep. 1998, pp. 4413-4415.
Sibanda et al, Experimental Design for the Formulation and Optimization of Novel Cross-Linked Oilispheres Developed for In Vitro Site-Specific Release of Mentha Piperita Oil, AAPS PharmSciTech, vol. 5, No. 1, 2004, Article 18, pp. 1-14.
Stackebrandt et al, Reclassification of *Amycolatopsis orientalis* Subsp. Lurida Lechevalier et al. 1986 as *Amycolatopsis lurida* sp. Nov., Comb. Nov., International Journal of Systematic and Evolutionary Microbiology, vol. 54, 2004, pp. 267-268.
Suarez et al, Morphological Characteristics of Colony Development in *Micromonospora chalcea*, Journal of Bacteriology, vol. 162, No. 3, Jun. 1985, pp. 1342-1344.
Suarez et al, Germination of Spores of *Micromonospora chalcea*: Physiological and Biochemical Changes, Journal of General Microbiology, vol. 121, 1980, pp. 159-167.
Tarhan et al, Variations of Vancomycin Production by *Amycolatopsis orientalis* Depending on the Glucose and Glycerol Concentrations as Carbon Sources, Trakya Univ. J. Sci., vol. 6, No. 2, 2005, pp. 108-115.
Igarashi et al, Revision of the Structure Assigned to the Antibiotic BU-4664L from *Micromonopora*, The Journal of Antibiotics, vol. 58, No. 5, 2005, pp. 350-352.
The Journal of Antibiotics, vol. 58, No. 7, Jul. 2005, p. C2, Correction to Igarashi et al, Revision of the Structure Assigned to the Antibiotic BU-4664L from *Micromonopora*, The Journal of Antibiotics, vol. 58, No. 5, 2005, pp. 350-352.

(Continued)

*Primary Examiner* — Susan Hanley
(74) *Attorney, Agent, or Firm* — Roylance, Abrams, Berdo & Goodman, L.L.P.

(57) ABSTRACT

The present invention provides a scalable process for producing a concentrate containing a mass of a farnesylated dibenzodiazepinone by fermenting in an aqueous culture medium a strain of a microorganism that is capable of producing the farnesylated dibenzodiazepinone, upon completion of fermentation harvesting the fermentation broth and extracting the fermentation broth to provide an extract, and thereafter treating the extract to form the concentrate. The concentrate so produced may be utilized in downstream processes for producing pharmaceutical compounds. A strain of a *Micromonospora* species capable of producing a farnesylated dibenzodiazepinone at a high yield rate is provided, together with culture media for culturing microorganisms, and fermentation conditions for production of the farnesylated dibenzodiazepinone of the concentrate.

13 Claims, 12 Drawing Sheets

OTHER PUBLICATIONS

Charan et al, Poster P:157, A New Antimicrobial Alkaloid from a *Micromonospora* Sp., 44th Annual Meeting of the American Society of Pharmacognosy, Jul. 12-16, 2003, Chapel Hill, NC.

Fiedler et al, Marine Actinomycetes as a Source of Novel Secondary Metabolites, Antonic van Leeuwenhock, vol. 87, 2005, pp. 37-42.

Bishop et al, Systematic Insertional Mutagenesis of a *Streptomycete* Genome: A Link Between Osmoadaptation and Antibiotic Production, Genome Research, 2004, vol. 14, No. 5, pp. 893-900.

Bushell et al, The Application of Materials Balancing to the Characterization of Sequential Secondary Metabolite Formation in *Streptomyces* cattleya NRRL 8057, Journal of General Microbiology, 1983, vol. 129, pp. 1733-1741.

Caldwell et al, The New Pre-Preclinical Paradigm: Compound Optimization in Early and Late Phase Drug Discovery, Current Topics in Medicinal Chemistry, 2001, vol. 1, No. 5, pp. 353-366.

Demain, Industrial Microbiology, Science, 1981, vol. 214, pp. 987-995.

Hosoya et al, Acquisition of Certain *Streptomycin*-Resistant (str) Mutations Enhances Antibiotic Production in Bacteria, Antimicrobial Agents and Chemotherapy, 1998, vol. 42, No. 8, pp. 2041-2047.

Hu et al, Novel Approach for Improving the Productivity of Antibiotic-Producing Strains by Inducing Combined Resistant Mutations, Applied and Environmental Microbiology, 2001, vol. 67, No. 4, pp. 1885-1892.

Jin et al, Production of Teicoplanin by Valine Analogue-Resistant Mutant Strains of *Actinoplanes teichomyceticus*, Applied Microbiology and Biotechnology, 2002, vol. 58, No. 1, pp. 63-66.

Kim et al, Mutagenesis of *Micromonospora rosaria* by Using Protoplasts and Mycelial Fragments, Applied and Environmental Microbiology, 1983, vol. 46, No. 3, pp. 689-693.

Lal et al, Rifamycins: Strain Improvement Program, Critical Reviews in Microbiology, 1995, vol. 21, No. 1, pp. 19-30.

Lee et al, Improved Production of Teicoplanin Using Adsorbent Resin in Fermentations, Letters in Applied Microbiology, 2003, vol. 37, No. 3, pp. 196-200.

Marshall et al, The Effect of Neutral Resins on the Fermentation Production of Rubradirin, Journal of Industrial Microbiology, 1990, vol. 5, No. 5, pp. 283-287.

Okamoto-Hosoya et al, Development of Antibiotic-Overproducing Strains by Site-Directed Mutagenesis of the rpsL Gene in *Streptomyces lividans*, Applied and Environmental Microbiology, 2003, vol. 69, No. 7, pp. 4256-4259.

Paradkar et al, Applications of Gene Replacement Technology to *Streptomyces clavuligerus* Strain Development for Clavulanic Acid Production, Applied and Environmental Microbiology, 2001, vol. 67, No. 5, pp. 2292-2297.

Parekh et al, Improvement of Microbial Strains and Fermentation Processes, Applied Microbiology and Biotechnology, 2000, vol. 54, No. 3, pp. 287-301.

Zhang et al, A Multi-Scale Study of Industrial Fermentation Processes and Their Optimization, Advances in Biochemical Engineering/Biotechnology, 2004, vol. 87, pp. 97-150.

Pfeifer et al, Process and Metabolic Strategies for Improved Production of *Escherichia coli*-Derived 6- Deoxyerythronolide B, Applied and Environmental Microbiology, 2002, vol. 68, No. 7, pp. 3287-3292.

Schmidt, Optimization and Scale Up of Industrial Fermentation Processes, Applied Microbiology and Biotechnology, 2005, vol. 68, No. 4, pp. 425-435.

Shima et al, Induction of Actinorhodin Production by rpsL (Encoding Ribosomal Protein S12) Mutations That Confer *Streptomycin* Resistance in *Streptomyces lividans* and *Streptomyces coelicolor* A3(2), Journal of Bacteriology, 1996, vol. 178, No. 24, pp. 7276-7284.

Stratigopoulos et al, Positive Control of Tylosin Biosynthesis: Pivotal Role of TylR, Molecular Microbiology, 2004, vol. 54, No. 5, pp. 1326-1334.

Tamehiro et al, Innovative Approach for Improvement of an Antibiotic-Overproducing Industrial Strain of *Streptomyces albus*, Applied and Environmental Microbiology, 2003, vol. 69, No. 11, pp. 6412-6417.

Thiry et al, Optimizing Scale-Up Fermentation Processes, Trends in Biotechnology, 2002, vol. 20, No. 3, pp. 103-105.

Tkacz et al, Improvement in the Titer of Echinocandin—Type Antibiotics: A Magnesium-Limited Medium Supporting the Biphasic Production of Pneumocandins Ao and B0, Journal of Industrial Microbiology, 1993, vol. 11, No. 2, pp. 95-103.

Torres-Bacete et al, Optimization of Culture Medium and Conditions for Penicillin Acylase Production by *Streptomyces lavendulae* ATCC 13664, Applied Biochemistry and Biotechnology, 2005, vol. 126, No. 2, pp. 119-132.

Dimitriadou et al, Identification and Characterization of a New Cytotoxic Agent from Actinomycetes (ECO-04601), AACR, Annual Meeting, Orlando, Florida, Mar. 27-31, 2004, p. 2060 (poster).

Clardy et al, Lessons from Natural Molecules, Nature, 2004, vol. 432, pp. 829-837.

* cited by examiner

PROCESS FOR PRODUCING FARNESYLATED DIBENZODIAZEPINONE BY FERMENTATION

The present application is a continuation of U.S. patent application Ser. No. 11/785,226, filed Apr. 16, 2007, which claims benefit under 35 U.S.C. §119(e) of U.S. provisional patent application No. 60/791,903, filed Apr. 14, 2006. The entire disclosure of each application is herein incorporated by reference.

FIELD OF INVENTION

The present invention relates to a process for preparing a concentrate comprising a mass of a farnesylated dibenzodiazepinone, namely ECO-4601, from a fermentation broth. The invention further relates to a concentrate comprising a mass of a farnesylated dibenzodiazepinone, namely ECO-4601, wherein said concentrate may be processed for the provision of a medicament for administration to a mammal in need of such medicament for the treatment of a disease condition such as cancer.

BACKGROUND

The compound ECO-04601 (hereinafter ECO-4601) is a novel farnesylated dibenzodiazepinone, namely 10-farnesyl-4,6,8-trihydroxy-dibenzodiazepin-11-one, having the structure of Formula I as shown below.

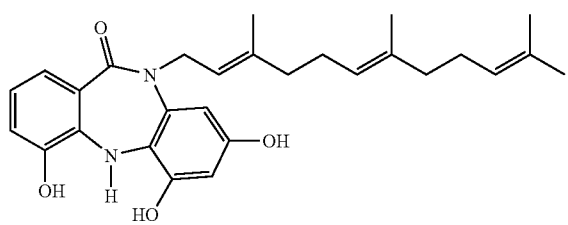

Formula 1

ECO-4601 has been isolated from fermentation cultures of a novel strain of the actinomycete *Micromonospora* sp. as disclosed in U.S. patent application Ser. No. 10/762,107 filed Jan. 21, 2004 (published Feb. 24, 2005 as US 2005-0043297 A1, issued as U.S. Pat. No. 7,101,872 on Sep. 5, 2006), also published Aug. 5, 2004 as PCT International Application WO2004/065591. The structure of ECO-4601 has been subsequently disclosed by Charan et al. (2004), *J. Nat. Prod.*, vol. 67, pages 1431-1433, the compound having been extracted from solids collected from a fermentation broth of *Micromonospora* strain DPJ12 that was isolated from the marine ascidian *Didemnum proliferum* Kott. at Shishijima Island, Japan. Charan et al. have referred to the isolated farnesylated dibenzodiazepinone as "diazepinomicin". The compound ECO-4601 has also been subsequently disclosed by Igarashi et al. (2005), *J. Antibiot.*, vol. 58, pages 350-352, this group having isolated the compound by extraction of a fermentation broth of a culture of an actinomycete, *Micromonospora* sp. TP-A086, that was isolated from a soil sample collected in Osawano, Japan. ECO-4601 has been shown to possess anti-bacterial and anti-cancer activities, and results from animal model studies indicate an in vivo anti-cancer potency of ECO-4601 (see U.S. patent application Ser. No. 10/951,436 filed Sep. 27, 2004 (published May 19, 2005 as US 2005-010736 A1, issued as U.S. Pat. No. 7,186,713 on Mar. 6, 2007), and U.S. patent application Ser. No. 11/130,295 filed May 16, 2005 (published Apr. 13, 2006 as US 2006-0079508 A1)).

Production of limited amounts of ECO-4601 via fermentation methods have been disclosed. U.S. patent application Ser. No. 11/130,295 discloses that ECO-4601 can be produced by inoculating a culture medium with a sample of a microorganism capable of producing ECO-4601, such as *Micromonospora* strain 046-ECO11 or strain [S01]046, and thereafter incubating the inoculated culture with aeration by agitation such as by shaking on a water bath or in a fermentor, or by injection of air, oxygen or an appropriate gaseous mixture into the culture medium. Incubation can last for a period of about 3 to 4 days at temperatures of about 18 to about 40° C., and at a pH of about 6 to about 9, in a suitable medium containing assimable sources of carbon, nitrogen, optional inorganic salts and other known growth factors. Upon completing cultivation, ECO-4601 can be isolated from the culture medium by techniques known in the art such as centrifugation, adsorption, chromatography, and filtration. Organic solvents such as ethyl acetate, n-butanol, n-butyl acetate or 4-methyl-2-pentanone may be mixed with the cultivated culture medium and the organic layer separated by centrifugation followed by solvent removal by evaporation to dryness, or by evaporation to dryness under a vacuum, to yield an ECO-4601 containing residue. Downstream purification can be performed by optionally reconstituting the residue with ethanol, ethyl acetate, methanol or a mixture thereof, and re-extraction in a two-phase system using a suitable organic solvent such as hexane, acetonitrile, ethyl acetate, methanol and carbon tetrachloride, methylene chloride or a mixture thereof, followed by further purification by techniques known in the art, such as chromatography.

Fermentation methods for producing limited amounts of the farnesylated dibenzodiazepinone of the present invention have been described in the art. For example, Igarashi et al. (supra) described a process wherein a 5 liter fermentation broth was extracted with 1-butanol and the organic layer concentrated in vacuo to yield an oily extract of 17 grams. Chromatographic purification (silica gel followed by LH-20) of the extract yielded 16 mg of light yellow needles. In Charan et al. (supra), a process was described wherein a 4 liter fermentation broth of *Micromonospora* DPJ12 was centrifuged and the resulting cell mass and HP20 resin (50 g/L of broth) were washed with water and extracted with methanol (3×250 mL). The combined methanol extracts were concentrated in vacuo and extracted with ethyl acetate (4×60 mL) to yield an extract of 278 milligrams. Further purification (Sephadex LH-20 column chromatography followed by reversed-phase HPLC) yielded 4.8 mg of the diazepinomicin product.

For development of ECO-4601 into a commercial pharmaceutical product, fermentation production of the compound will be required on a scale(s) to generate quantities of the compound to meet sufficiently supply requirements for clinical trial testing regimens, and thereafter for subsequent commercial manufacturing of formulations and dosages that will be prescribed to patients in need of treatment. As such, there remains the need for a robust and commercially-practical fermentation process pertaining to the fermentation of *Micromonospora* sp. for the production of quantities of ECO-4601 useful for clinical trials and commercial production of pharmaceutical products. Advantageously, the fermentation process should provide several benefits in terms of being scalable from a laboratory level to various levels commercial production, while concomitantly not requiring an increased number of fermentation vessels or other pieces of equipment and/or steps involved in downstream processing and purification steps, nor require increased volumes of an extraction solvent or solvents beyond that directly proportional to an increased fermentation volume. As well, there exists a need for a fermentation process for the production of ECO-4601 that provides for a high yield rate of the compound from a fermentation broth, and which allows for the compound to be efficiently extracted from the fermentation broth and provided in a form, preferably a concentrated form, that is stable, easily transportable, and which can thereafter be easily subjected to downstream processing for production of crystalline forms of ECO-4601 that may thereafter be formulated into pharmaceutically-acceptable compositions for use in patients requiring need of such compositions.

SUMMARY OF THE INVENTION

The present invention provides a process for recovering and concentrating a farnesylated dibenzodiazepinone of structural Formula I Formula I

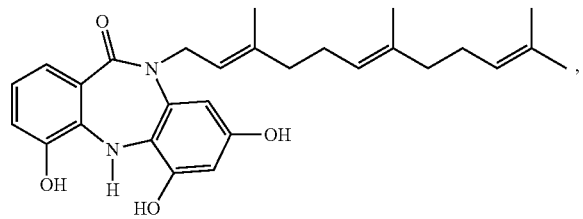

comprising the steps of: a) fermenting a strain of a microorganism capable of producing said farnesylated dibenzodiazepinone in an aqueous culture medium thereby producing a fermentation broth comprising said farnesylated dibenzodiazepinone of structural Formula I; b) adjusting said fermentation broth to allow said farnesylated dibenzodiazepinone to associate with a particulate matter present in said broth; c) harvesting said particulate matter from said broth for obtaining a harvested particulate matter; d) extracting said harvested particulate matter with a volume of a suitable organic solvent in a proportion of about 2:1 to about 5:1 to said harvested particulate matter to thereby form an extract; and e) treating said extract to form a first concentrate comprising said farnesylated dibenzodiazepinone, wherein said first concentrate comprises said farnesylated dibenzodiazepinone at a concentration greater than about 50-fold than said farnesylated dibenzodiazepinone in said fermentation broth of a), and wherein said farnesylated dibenzodiazepinone is recovered from said fermentation broth of a) in an amount of at least about 50% of the amount of said farnesylated dibenzodiazepinone in said fermentation broth. In yet another aspect, the process of the present invention further comprises processing said first concentrate in order to reduce a level of an impurity in said first concentrate to thereby produce a second concentrate. In one aspect of the present invention, the second concentrate is substantially free of molecules other than the farnesylated dibenzodiazepinone of Formula I. In yet a still further aspect, the process of the present invention even further comprises a step of crystallizing from said second concentrate the farnesylated dibenzodiazepinone of Formula I to thereby produce a crystalline farnesylated dibenzodiazepinone of Formula I suitable for use in the preparation of a pharmaceutical formulation.

In yet a further aspect of the present invention, the farnesylated dibenzodiazepinone is recovered from said fermentation broth of a) in an amount of at least about 60% of the amount of said farnesylated dibenzodiazepinone in said fermentation broth, and in yet another aspect the farnesylated dibenzodiazepinone is recovered from said fermentation broth of a) in an amount of at least about 65% of the amount of said farnesylated dibenzodiazepinone in said fermentation broth.

In yet another aspect of the process of the present invention, the particulate matter comprises the fermented microorganism present in the fermentation broth. In still yet a further aspect of the process of the present invention, the particulate matter further comprises an adsorbent resin. In yet another aspect of the process of the present invention, the fermentation broth is adjusted to a pH value of about 2 to about 4, and in yet another aspect of the process of the present invention, the fermentation broth is further adjusted to a temperature range of about 2° C. to about 10° C., while in yet another aspect of the process of the present invention, the fermentation broth is maintained at the temperature range for a period of about 16 hours to about 72 hours. In still yet another aspect of the process of the present invention, the fermentation is completed in from about 48 hours to about 110 hours.

In a still further aspect of the process of the present invention, the microorganism is a bacterium, and still further, the bacterium is an Actinomycete, and yet further the Actinomycete is a *Micromonospora, Streptomyces* or a *Rhodococcus* species, and yet further the Actinomycete is *Micromonospora* sp. [S01]046 having IDAC accession number 231203-01 or *Micromonospora* sp. [S01U02]046 having IDAC accession number 070905-01.

In a further aspect of the process of the present invention, the suitable organic solvent comprises at least one lower alkyl alcohol, and in a further aspect the lower alkyl alcohol is methanol, or ethanol, or propanol, or iso-propanol or butanol or a mixture of two of these lower alkyl alcohols. In yet a further aspect, the suitable organic solvent is ethyl acetate or acetonitrile.

In another aspect of the process of the present invention, the aqueous culture medium in which the strain of the microorganism is fermented is AP, CA, DZ, GP, HI, JA, MI, PI, QI, QP or YB, and in yet another aspect the aqueous culture medium is QB, MA, KH, RM, JA, FA, or HI.

In another aspect of the process of the present invention, the harvesting of the particulate matter from the broth is performed using an ultrafiltration system, and in yet another aspect, the ultrafiltration system has one or more filter elements having a pore size of about 0.2 to about 0.45 micrometers. In a still further aspect of the process of the present invention, the harvesting of the particulate matter from the broth is performed by centrifugation.

In another aspect of the process of the present invention, the extraction of the harvested particulate matter comprises one to three rounds of extraction using the suitable organic solvent, and in yet a further aspect, the extraction further comprises circulating the particulate matter together with the suitable organic solvent in a system at a flow rate of about 30 Hz to about 50 Hz, and at a temperature of about 39° C. to about 45° C., and yet still further, the circulation is for a period of about 50 minutes to about 120 minutes. In yet a further aspect, the extraction comprises subjecting the particulate matter together with the suitable organic solvent to a centrifugation treatment. In yet a still further aspect of the process of the present invention, the volume of the suitable organic solvent utilized for the extraction is calculated in proportion to the harvested particulate matter mass (volume: mass) or in proportion to the harvested particulate matter volume (volume:volume).

In another aspect of the process of the present invention, the treating of the extracted, harvested particulate matter is an evaporation treatment, and in yet a further aspect, the evaporation treatment is conducted under a reduced pressure, and in yet a further aspect, the evaporation is performed while incubating the extract with an adsorbent resin, for example, HP20 resin and wherein evaporation treatment is conducted under a reduced pressure.

In another aspect of the process of the present invention, the treating of the extracted, harvested particulate matter comprises incubating the extract with an absorbent resin to form a mixture, followed by an addition of water to the mixture to displace the farnesylated dibenzodiazepinone of Formula I onto the resin. In yet a further aspect, the adsorbent resin mixed with the extract is provided in a ratio (W/W) of about 10 times to about 40 times to the farnesylated dibenzodiazepinone of Formula I in the extract. In yet another aspect of the process of the present invention, the water is added to the mixture at a volumetric rate (V/V) of about 0.5% to about 20% of the volume of the mixture, and in yet another aspect, volume flow rate is about 0.5% to about 5% of the volume of the mixture. In a still further aspect, the water added to the mixture is of a total volume of about 1.0 to about 1.5 times the volume of the mixture, and in yet a further aspect, the total volume of water added to the mixture is of about 1.2 to about 1.5 times the volume of the mixture.

In a further embodiment, the present invention provides for a concentrate comprising the farnesylated dibenzodiazepinone of structural Formula I Formula I

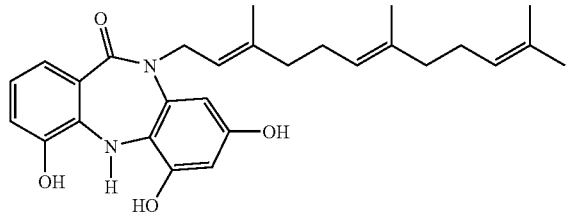

wherein said concentrate is obtained according to the method of the present invention.

In another aspect, the concentrate that is provided by the present invention comprises the farnesylated dibenzodiazepinone of Formula I, wherein the farnesylated dibenzodiazepinone of Formula I is recovered from said fermentation broth of a) in an amount of at least about 60% of the amount of said farnesylated dibenzodiazepinone in said fermentation broth, and in yet another aspect the farnesylated dibenzodiazepinone of Formula I is recovered from said fermentation broth of a) in an amount of at least about 65% of the amount of said farnesylated dibenzodiazepinone in said fermentation broth.

In a further embodiment, the present invention provides for a microorganism capable of producing, during a fermentation period in a volume of an aqueous culture medium, a farnesylated dibenzodiazepinone of structural Formula I Formula I

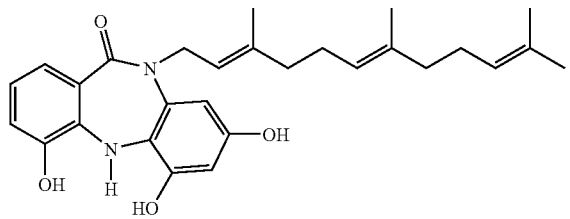

at a yield rate of about 0.073 mg/L/hour to about 5.06 mg/L/hour as averaged over the fermentation period. In a further aspect of the present invention, the yield rate of the microorganism is of about 2.15 mg/L/h to about 5.06 mg/L/h as averaged over the fermentation period, and in yet a still further aspect of the present invention, the yield rate of the microorganism is of about 3.00 mg/L/h to about 5.06 mg/L/h as averaged over the fermentation period. In a further aspect, the microorganism is a bacterium, and even more particularly, the bacterium is an Actinomycete, and even still more particularly, the Actinomycete is a *Micromonospora*, *Streptomyces* or a *Rhodococcus* species, and still more particularly, the Actinomycete is *Micromonospora* sp. [S01]046 having IDAC accession number 231203-01 or *Micromonospora* sp. [S01U02]046 having IDAC accession number 070905-01.

In yet a further embodiment, the invention provides for an Actinomycete species, namely, *Micromonospora* sp. [S01U02]046, having IDAC accession number 070905-01.

In a further embodiment, the present invention provides for various culture medium compositions for culturing bacteria, and methods for culturing bacteria, and in which in yet another aspect of the present invention such media and methods may be utilized for growing bacteria under aqueous conditions, for example, so as to produce a fermentation broth culture. In one aspect, the culture medium composition comprises 10 g/L glucose, 20 g/L soluble starch, 5 g/L yeast extract, 5 g/L Bacto-peptone and 2 g/L $CaCO_3$. In another aspect, the culture medium composition comprises 10 g/L glucose, 40 g/L potato dextrin, 5 g/L yeast extract, 5 g/L Bacto-peptone and 2 g/L $CaCO_3$. In another aspect, the culture medium composition comprises 10 g/L glucose, 25 g/L soluble starch, 5 g/L yeast extract, 5 g/L Bacto-peptone and 3 g/L $CaCO_3$. In yet still another aspect, the culture medium comprises 12 g/L glucose, 10 g/L potato dextrin, 5 g/L corn steep liquor, 10 g/L Pharmamedia and 4 g/L Proflo oil. In yet a still further aspect, the culture medium comprises 20 g/L potato dextrin, 8.34 g/L yeast extract, 30 g/L glycerol, 2.5 g/L Bacto-peptone and 3 g/L $CaCO_3$.

BRIEF DESCRIPTION OF THE FIGURES

FIGS. 1 to 4: show the different steps involved in the biosynthetic pathway of ECO-04601. Each of FIGS. 1 to 4 shows the three biosynthetic loci A, B and C where ORFs are represented by arrows. Highlighted ORFs are involved in the steps described in the schematic diagram. The biosynthetic enzymes involved in the steps depicted in schematic diagrams are indicated by their family designation and the respective ORF number in each of Loci A, B and C (e.g., 8/7/7).

DETAILED DESCRIPTION OF THE INVENTION

Figure 1A:
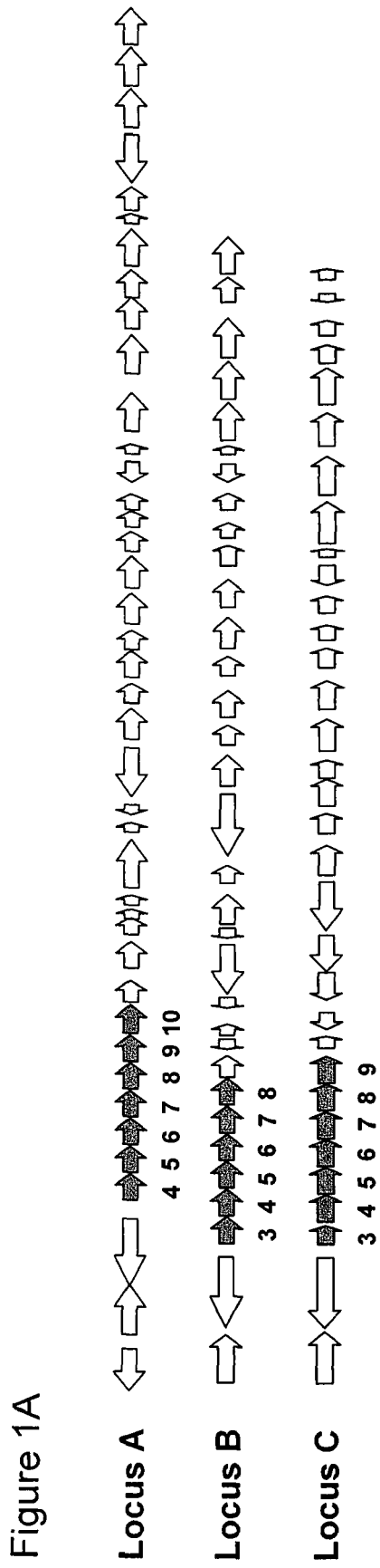
FIGS. 1A and 1B show, respectively, the three biosynthetic loci A, B and C wherein the ORFs represented by highlighted arrows (FIG. 1A) are involved in the steps of the biosynthetic pathway for the production of farnesyl-diphosphate, and schematic diagram (FIG. 1B) of the biosynthetic pathway for the production of farnesyl-diphosphate, providing the farnesyl group of ECO-04601.
Figure 1B:
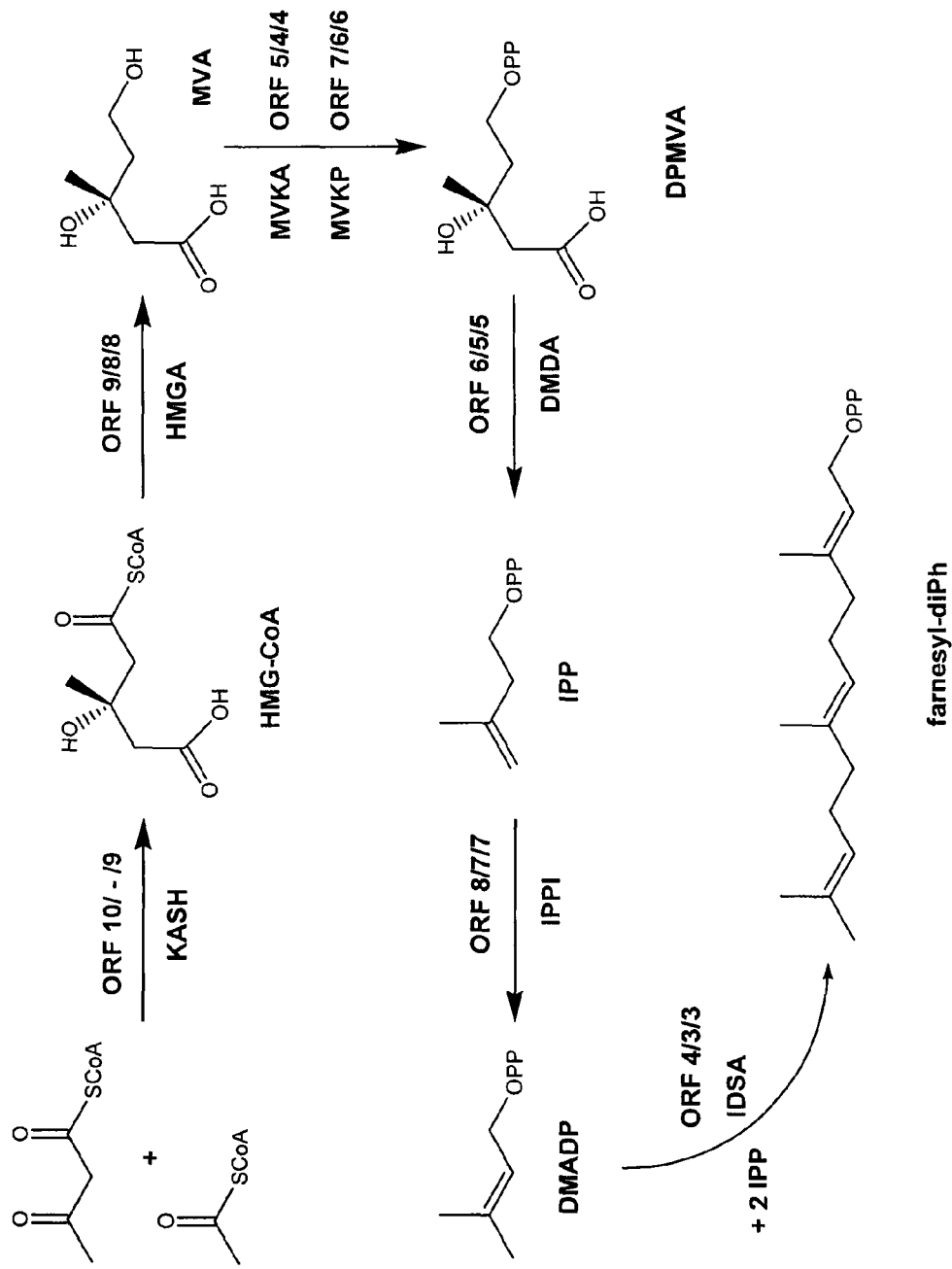
Figure 2A:
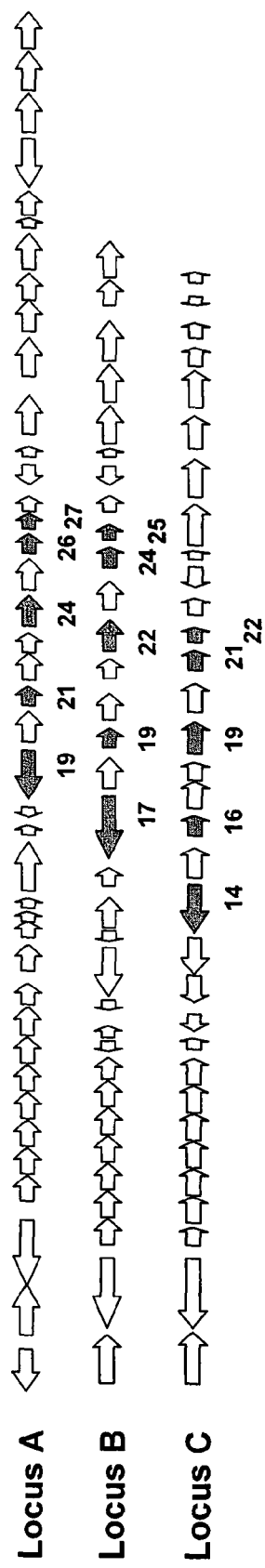
FIGS. 2A and 2B show, respectively, the three biosynthetic loci A, B and C wherein the ORFs represented by highlighted arrows (FIG. 2A) are involved in the steps of the biosynthetic pathway for the production of the 3-hydroxy-anthranalite-adenylate precursor of the dibenzodiazepinone group, and a schematic diagram (FIG. 2B) of the biosynthetic pathway for the production of 3-hydroxy-anthranilate-adenylate precursor of the dibenzodiazepinone group.
Figure 2B:
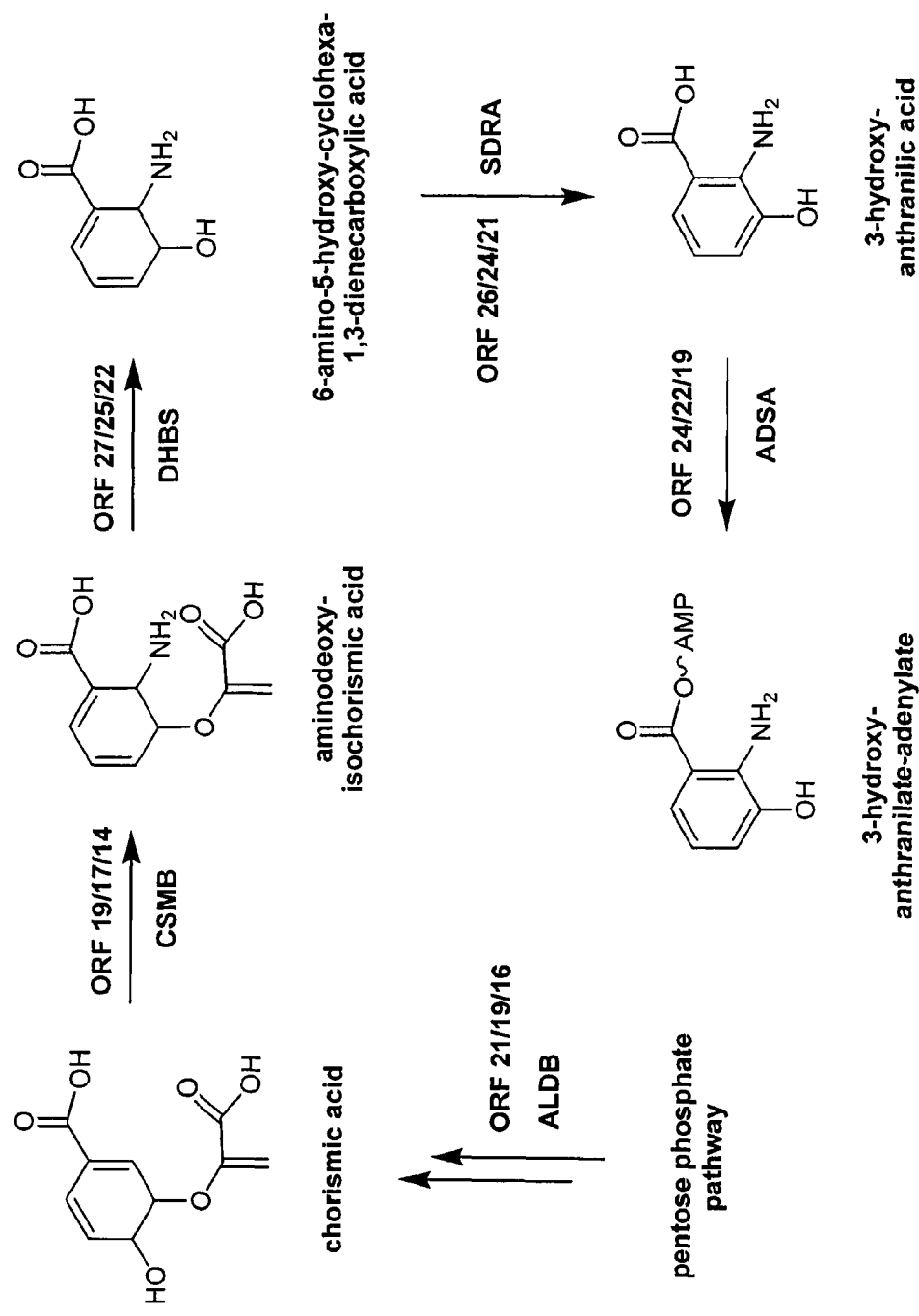
Figure 3A:
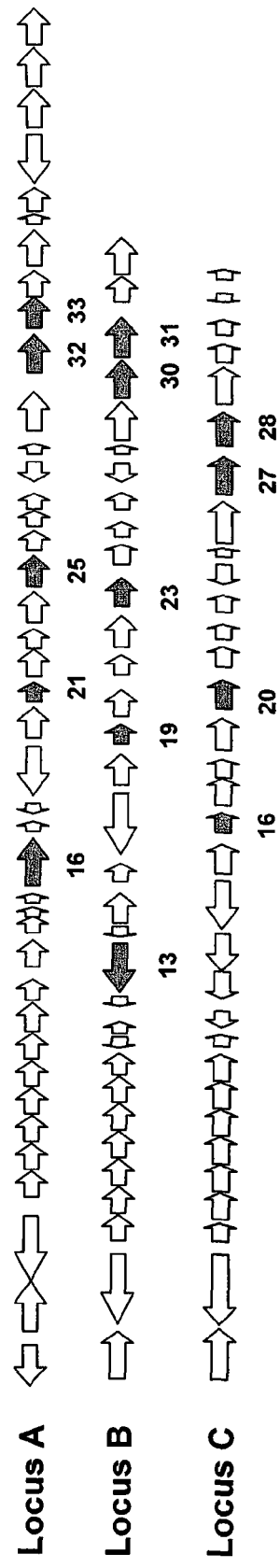
FIGS. 3A and 3B show, respectively, the three biosynthetic loci A, B and C wherein the ORFs represented by highlighted arrows (FIG. 3A) are involved in the steps of the biosynthetic pathway for the production of the 2-amino-6-hydroxy-[1,4] benzoquinone precursor of the core dibenzodiazepinone group, and a schematic diagram (FIG. 3B) of the biosynthetic pathway for the production of 2-amino-6-hydroxy-[1,4]benzoquinone precursor of the core dibenzodiazepinone.
Figure 3B:
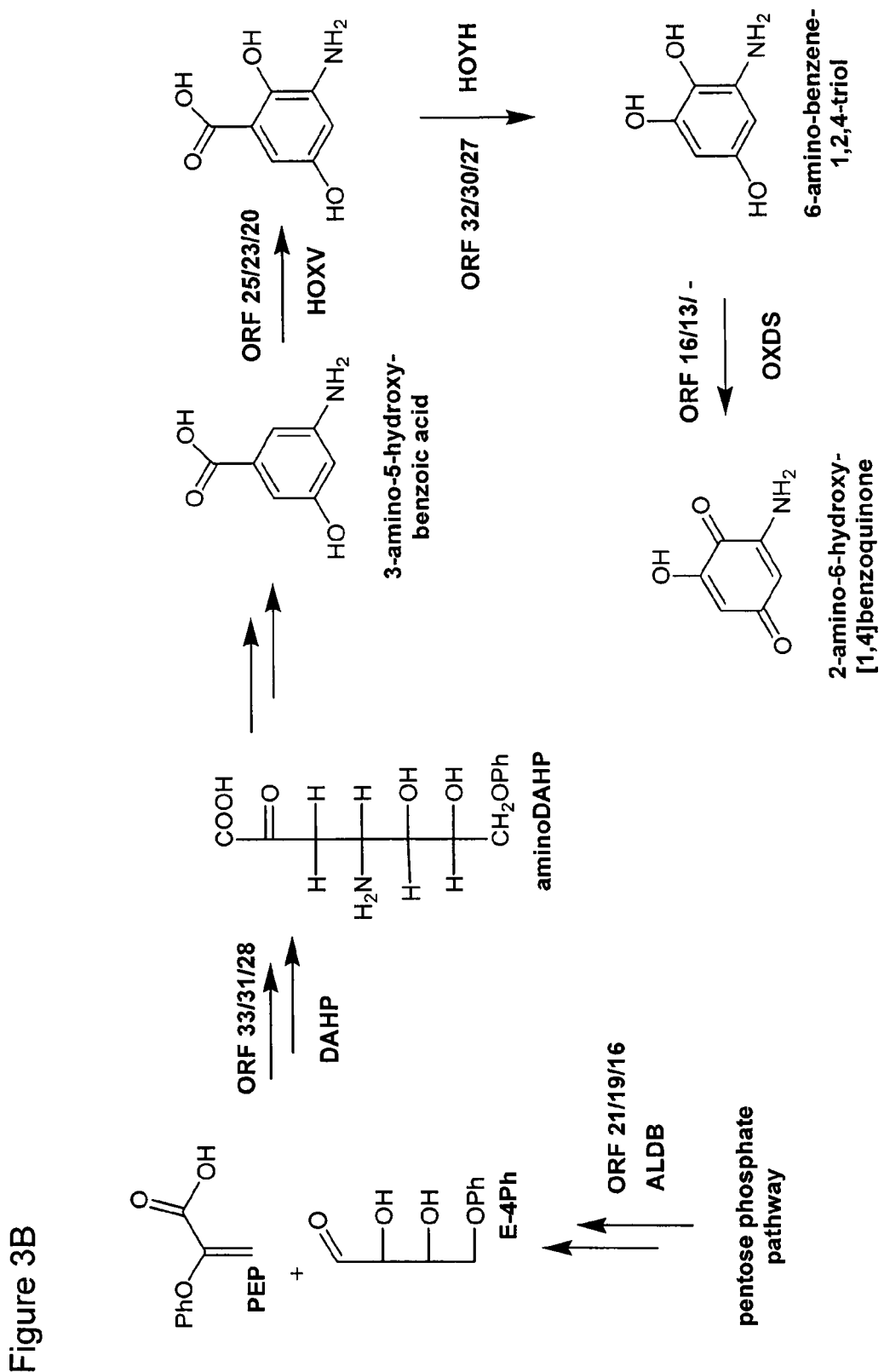
Figure 4A:
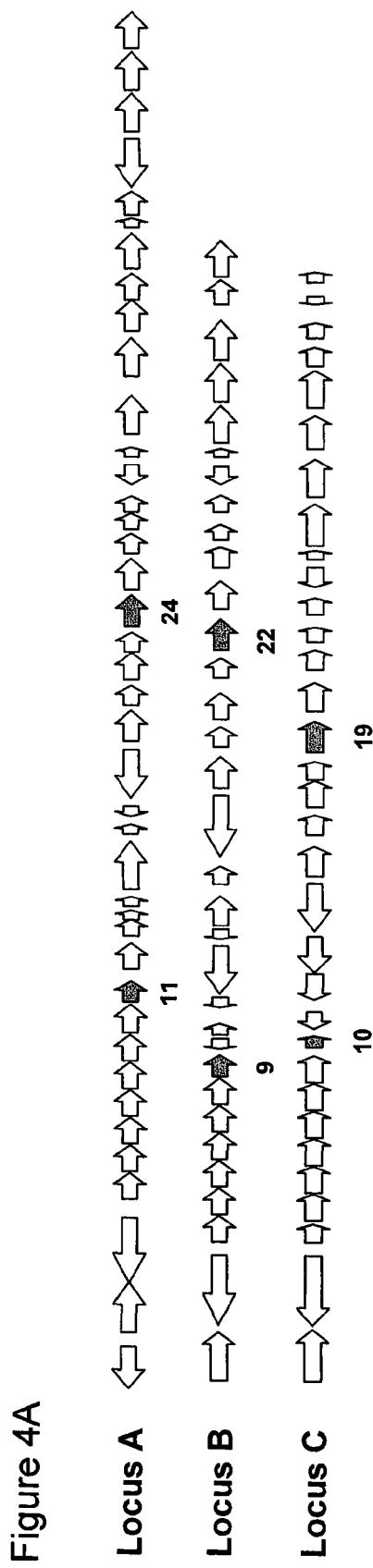
FIGS. 4A and 4B show, respectively, the three biosynthetic loci A, B and C wherein the ORFs represented by highlighted arrows (FIG. 4A) are involved in the steps of the biosynthetic pathway for the assembly of the ECO-04601 precursors farnesyl-diphosphate, 3-hydroxy-anthranalite-adenylate and 2-amino-6-hydroxy-[1,4]benzoquinone, and a schematic diagram (FIG. 4B) of the biosynthetic pathway for the assembly of the ECO-04601 precursors, farnesyl-diphosphate, 3-hydroxy-anthranilate-adenylate and 2-amino-6-hydroxy-[1,4] benzoquinone.
Figure 4B:
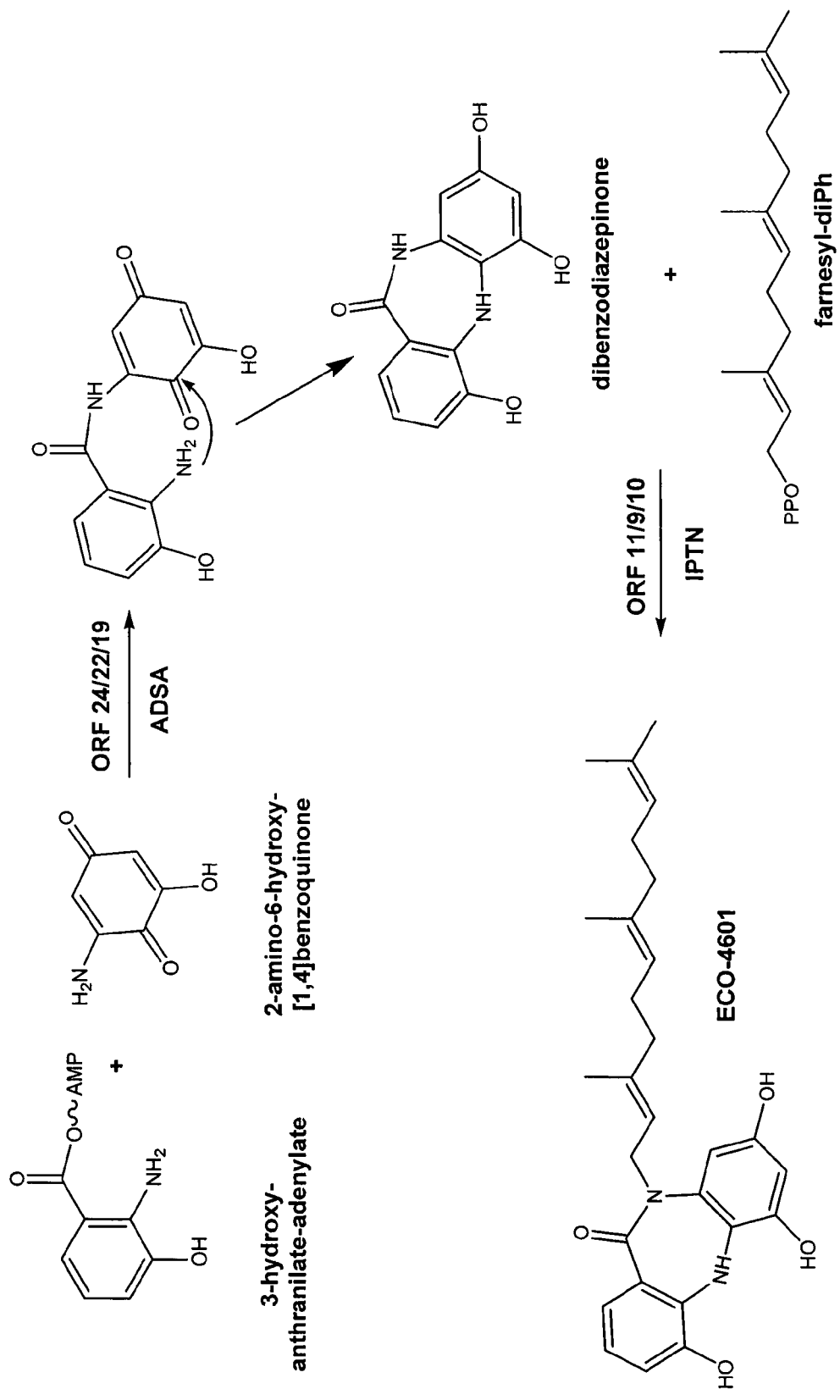

The present invention provides a scalable process for the fermentation production of a farnesylated dibenzodiazepinone

I. DEFINITIONS

Unless otherwise defined all technical and scientific terms used herein have the meaning as commonly understood by a person skilled in the art to which this invention belongs.

For convenience, the meaning of certain terms and phrases used in the specification, examples, and appended claims are provided below.

As used herein, the term "farnesylated dibenzodiazepinone" refers to a class of dibenzodiazepinone compounds containing a farnesyl moiety. The term includes, but is not limited to, the exemplified compound of the present invention, 10-farnesyl-4,6,8-trihydroxy-dibenzodiazepin-11-one, which is referred to herein as "ECO-04601". As used herein, the term "farnesylated dibenzodiazepinone" includes compounds of this class that can be used as intermediates in chemical syntheses.

As used herein, the term "concentrate" refers to a liquid, a semi-solid or a solid mass comprising, in part, a mass of a farnesylated dibenzodiazepinone, namely ECO-4601. If in the form of a semi-solid or solid mass, the concentrate may be substantially free of water and/or substantially free of any solvent or solvents utilized to produce the concentrate. It is to be understood that the concentrate may take a form of a highly viscous paste, whether in a semi-solid or solid form. A concentrate in a solid form that is substantially free of any liquid or liquids may be provided mixed with an adsorbent resin.

As used herein the term "first concentrate" refers to a concentrate comprising, in part, the farnesylated dibenzodiazepinone of Formula I, namely ECO-4601, wherein said first concentrate is formed by treating an extract of a fermentation broth comprising the farnesylated dibenzodiazepinone of Formula I. The first concentrate, or a combination of such first concentrates, may thereafter be subjected to processing for reducing a level of an impurity present in the first concentrate, for example by being processed in a column cleanup procedure comprising at least one round of cleanup, and so as to result in the formation of a second ($2^{nd}$) concentrate comprising the farnesylated dibenzodiazepinone of Formula I. The second concentrate may be substantially free of other molecules other than the farnesylated dibenzodiazepinone of Formula I. The second concentrate may thereafter be subjected to a crystallization process for producing crystalline ECO-4601 suitable for use in the preparation of a pharmaceutical formulation or formulations.

As used herein, the term "ratio (W/W)" refers to a ratio of two masses in relative proportion to each other. Preferably, the term refers to a mass of a farnesylated dibenzodiazepinone, namely ECO-4601, present in a concentrate relative to a mass of ECO-4601 present in a fermentation broth. Further, the term "ratio (W/W)" includes, and is interchangeable with, the expression of such a ratio in terms of a percentage of the two masses relative to each other, for example, by expression of a mass of ECO-4601 present in a concentrate as a percentage of a mass of ECO-4601 present in a fermentation broth or combined fermentation broths. The fermentation broth may be a single broth, or may be a combination of two or more separate fermentation broths that have been combined prior to being extracted. It is to be understood that equivalent mass units will be employed in describing an amount of ECO-4601 present in the concentrate relative to the mass of ECO-4601 present in the fermentation broth, for example, micrograms ($\mu$g) to micrograms ($\mu$g), milligrams (mg) to milligrams (mg), grams (g) to grams (g), or kilograms (kg) to kilograms (kg). As such, it is to be understood that the mass units utilized to express the ratio (W/W) are not restricted to a particular order or size of units (e.g. only kg), and that all are understood to be included when referring to a ratio W/W of weight of ECO-4601 in the concentrate (a second mass) to weight of ECO-4601 in the fermentation broth (a first mass).

As used herein, a "strain" means a cell or population of cells that has the same general characteristics of a given type of organism, for example a bacterium, or of a particular genus, species, and serotype. If the strain comprises a population of cells, it will be recognized by those of skill in the art that the population will be descendant from a single organism or pure culture isolate.

As used herein, the term "microorganism capable of producing a farnesylated dibenzodiazepinone" refers to a microorganism that carries genetic information necessary to produce a farnesyl dibenzodiazepinone compound, whether or not the organism naturally produces the compound. The terms apply equally to organisms in which the genetic information to produce the farnesyl dibenzodiazepinone compound is found in the organism as it exists in its natural environment, and to organisms in which the genetic information is introduced by recombinant techniques. Specific organisms contemplated herein include, without limitation, organisms of the family Micromonosporaceae, of which preferred genera include *Micromonospora*, *Actinoplanes* and *Dactylosporangium*; the family Streptomycetaceae, of which preferred genera include *Streptomyces* and *Kitasatospora*; the family Pseudonocardiaceae, of which preferred genera are *Amycolatopsis* and *Saccharopolyspora*; the family Actinosynnemataceae, of which preferred genera include *Saccharothrix* and *Actinosynnema*; and species of the genus *Rhodococcus*; however the terms are intended to encompass all organisms containing genetic information necessary to produce a farnesyl dibenzodiazepinone compound. A preferred producer of a farnesyl dibenzodiazepinone compound includes *Micromonospora* sp. strain [S01U02]046, a deposit of which was made on Sep. 7, 2005, with the International Depository Authority of Canada (IDAC), Bureau of Microbiology, Health Canada, 1015 Arlington Street, Winnipeg, Manitoba, Canada R3E 3R2, under Accession No. IDAC 070905-01.

As used herein, an "aqueous medium" means a medium containing one more sources of assimable carbon, nitrogen and inorganic salts and which is capable of supporting growth of a microorganism capable of synthesizing ECO-4601.

As used herein, the term "adjusting" refers to a change induced, upon completion of a fermentation culture period, in one or more of a physical or a chemical condition or conditions of a fermentation broth comprising a farnesylated dibenzodiazepinone. An adjustment of a chemical condition of the fermentation broth includes, but is not limited to, inducing an acidification of the fermentation broth. An adjustment of a physical condition of the fermentation broth includes, but is not limited to, a reduction in the temperature of the fermentation broth. Any particular adjustment may be accomplished using techniques or reagents known in the art, for example, different mechanical means for lowering the temperature of a fermentation broth. The term is to equally apply to the adjusting of a condition or conditions that occurs by a series of graded or step-wise adjustments versus a single adjustment. As well, the term is to be understood to include the contemporaneous adjustment of more than one condition, whether or not the adjustment of each condition occurs by a series of graded or step-wise adjustments versus a single adjustment.

As used herein, the term "a particulate matter" refers to minute particles of one or more types that are present in the fermentation broth comprising the farnesylated dibenzodiazepinone. The term includes, but is not limited to, the microorganism that is capable of producing the farnesylated dibenzodiazepinone, and which by default would be present in the fermentation broth. It is to be understood that the term equally applies to an adsorbent resin that would be capable of binding at least the farnesylated dibenzodiazepinone. The adsorbent resin may be present in the fermentation broth upon initiation of the fermentation process, or may be added to the fermentation broth upon expiry of an allotted time or upon the fermentation broth reaching a pre-determined condition such as, for example, a particular degree of density or age. A number of types of adsorbent resins are known in the art and may be used in the present invention. Such resins include, but are not limited to, XAD 2, XAD 4, XAD 7, XAD 8 and XAD 16 (Rohm and Haas); HP20, HP20S, HP20SS and SP70 (the adsorbent resin DIAION®); and reverse phase silicas such as C-8, C-10 and C-18.

As used herein, the term "associate with" refers to a chemical or physical interaction that may occur between a molecule of a farnesylated dibenzodiazepinone and a surface or surfaces of a particulate matter present in a fermentation broth such that the farnesylated dibenzodiazepinone is retained or substantially retained by the particulate matter. The term includes, but is not limited to, weak interactions that may occur between molecules of the farnesylated dibenzodiazepinone and a surface of a particulate matter present in the fermentation broth, for example, hydrogen bonding, electrostatic attractions, van der Waals bonding, hydrophobic attractions, or partitioning. The term will be understood to include the adsorption of the farnesylated dibenzodiazepinone by a synthetic adsorbent resin, such as for example, DIAION® HP20 adsorbent resin.

As used herein, the term "suitable organic solvent" refers to an organic solvent in which the farnesylated dibenzodiazepinone, namely ECO-4601, is readably soluble. By readily soluble, it is meant that the solvent will dissolve a mass of ECO-4601 in sufficient concentration that a volume of the solvent required to extract a slurry provided from the ECO-4601-containing fermentation broth of the present invention will be in a range of about twice to about five times of a volume of the slurry. It will be understood that the term equally applies to a mixture of organic solvents in which the farnesylated dibenzodiazepinone, namely ECO-4601, is readably soluble. A choice of a particular suitable organic solvent, or a mixture of suitable organic solvents, for extracting the farnesylated dibenzodiazepinone from the slurry may be dependent upon a number of factors in combination with the solubility of the farnesyl dibenzodiazepinone in the solvent, and such factors may include but are not limited to a solvent's cost, availability, ease of handling, environmental impact, hazardous potential (e.g. explosivity) and disposability. As will be appreciated by those of skill in the art, a number of different suitable organic solvents may be selected. Preferably, the suitable organic solvent would be a one-carbon to a four-carbon solvent, or an aromatic solvent. More preferably, the suitable organic solvent or mixture of suitable organic solvents would be selected from one or more the solvent families or particular solvents, as follows: lower alkyl alcohols (e.g., methanol, ethanol, propanol, n-butanol, iso-propanol, propylene glycol); acetonitrile; toluene; oxygen-containing organic solvents such as dialkyl ketones (e.g. acetone, 2-butanone), tetrahydrofuran, dioxane, alkyl acetates (e.g. ethyl acetate, iso-propyl acetate, butyl acetate); and dialkyl ethers (e.g. di-isopropyl ether, tert-butyl methyl ether).

As used herein, the term "volume of a suitable organic solvent in a proportion" refers to a volumetric amount of a solvent as measured in relation to a mass or a volume of the solute that is to be mixed with the solvent. It is to be understood that for the purpose of the present invention, equivalent volume units will be employed in describing a volume of suitable organic solvent relative to a volume or a mass of a particulate matter that is harvested from a fermentation broth. For example, for a 1 L volume of particulate matter, a 3 L volume of the suitable organic solvent would be utilized, and if a 100 gram mass of particulate material was harvested from the fermentation broth a 300 mL volume of the suitable organic solvent would be utilized. As will be appreciated by those of skill in the art, the harvested particulate matter may be subjected to two or more rounds of extraction with an equal or non-equal volumes of the suitable organic solvent, solvents, or mixtures thereof, per extraction. Further, it will be understood by those of skill in the art, that the suitable organic solvent may be a mixture of two or more organic solvents, provided that the farnesylated dibenzodiazepinone, namely ECO-4601, is soluble in the mixture.

As used herein, the term "treating" refers to the subjection of an extract of the present invention to a physical or chemical treatment or a combination thereof. The physical or chemical treatment, or combination thereof, may occur in the form of a physical or chemical process that is applied to the extract, wherein the process in part requires an incubation of the extract with one or more particular substances. The physical or chemical treatment, or combination thereof, should be sufficient to achieve a removal or a substantial removal of the suitable organic solvent, solvents, or mixtures thereof from the extract. The term includes, but is not limited to, an evaporation process, preferably when said evaporation process is conducted under a reduced pressure, and more preferably when said evaporation process is conducted in conjunction with a warming of the extract. Further, the term includes an addition of an adsorbent resin to the extract, whether such addition is an alternative to or in conjunction with the subjection of the extract to an evaporation process. As well, the term includes a microfiltration to remove a bulk of the solvent, followed by evaporation to dryness. As well, the term includes a centrifugation to separate, for example, mycelia from a fermentation broth and also to aid in an extraction of a farnesylated dibenzodiazepinone from mycelia in the presence of the solvent.

As used herein, the term "displacement" means to move or shift an object or molecule(s), for example molecules of a farnesylated dibenzodiazepinone, from an environment or condition to a different environment, condition, or state, and may include a change in the physical or chemical state of such a molecule(s), for example, by performance of a step or series of steps, whether such step or steps is/are a mechanical or chemical step, so as to induce a removal of such molecule(s) from a solution or slurry. Removal of such molecule(s) from solution may be achieved, for example, by displacement of such molecule(s) from a solution or slurry onto an adsorbent resin.

As used herein, the term "substantially free of other molecules" means a concentrate or compound or mixture comprising the farnesylated dibenzodiazepinone of Formula I that is at least 60%, at least 70%, at least about 80%, at least about 90%, at least about 91%, at least about 92%, at least about 93%, at least about 94%, at least about 95%, at least about 96%, at least about 97%, at least about 98%, at least about 99% of 100% pure farnesylated dibenzodiazepinone of Formula I, measured by weight.

II. PRODUCTION OF A FARNESYLATED DIBENZODIAZEPINONE BY FERMENTATION

A. Microorganisms, Genes and Recombinant Microorganisms i) Microorganisms

The farnesyl dibenzodiazepinone compounds of the present invention may be biosynthesized by various microorganisms. Microorganisms that may synthesize the compounds of the present invention include but are not limited to bacteria of the order Actinomycetales, also referred to as actinomycetes. Non-limiting examples of members belonging to the genera of Actinomycetes include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium*, and *Actinomadura*. The taxonomy of actinomycetes is complex and reference is made to Goodfellow, *Suprageneric Classification of Actinomycetes* (1989); *Bergey's Manual of Systematic Bacteriology*, Vol. 4 (Williams and Wilkins, Baltimore, pp. 2322-2339); and to Embley and Stackebrandt, "The molecular phylogeny and systematics of the actinomycetes," *Annu. Rev. Microbiol.* (1994) 48:257-289, each of which is hereby incorporated by reference in its entirety, for genera that may synthesize the compounds of the invention.

Preferably, a microorganism that is to be used for the fermentation production of ECO-4601 according to the process of the present invention will have inherent to the microorganism the genetic information necessary to allow for the microorganism to biosynthesize the compound. Preferably, the microorganism is a *Micromonspora* species, more preferably *Micromonspora* sp 046-EC011 a deposit of which was made on Mar. 7, 2003, with the International Depository Authority of Canada (IDAC), Bureau of Microbiology, Health Canada, 1015 Arlington Street, Winnipeg, Manitoba, Canada R3E 3R2, under Accession Number IDAC 070303-01; more preferably *Micromonspora* sp [S01]046, a deposit of which was made on Dec. 23, 2003, with the International Depository Authority of Canada (IDAC), Bureau of Microbiology, Health Canada, under Accession Number IDAC 231203-01; more preferably a *Micromonospora* strain that has been selected for its ability to overproduce ECO-4601, and most preferably *Micromonospora* strain [S01U02]046, a deposit of which was made on Sep. 7, 2005, with the International Depository Authority of Canada (IDAC), Bureau of Microbiology, Health Canada, 1015 Arlington Street, Winnipeg, Manitoba, Canada R3E 3R2, under Accession Number IDAC 070905-01, and *Micromonospora echinospora challisensis* NRRL 12255 and *Streptomyces carzinostaticus neocarzinostaticus* ATCC 15944.

The deposit of the deposited strains has been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112. A license may be required to make, use or sell the deposited strains, and compounds derived therefrom, and no such license is hereby granted.

Methods for generating strains of microorganisms capable of biosynthesizing increased levels of a particular bioactive compound under defined fermentation conditions, for example a compound that possesses an antibiotic activity or an anticancer activity, are known in the art. Such methods may rely upon the selection of a mutant strain generated as a result of a naturally-occurring mutation or by a mutation that is induced due to treatment with a mutagenic agent. Examples of suitable mutagenic agents include, but are not limited to, N-methyl-N'-nitro-N-nitroso-guanidine, ethylmethansulfonate, nitrous acid, ultraviolet irradiation, X-rays and gamma irradiation, a combination of UV and psoralen, and transposon mutagenesis. Protocols and parameters for the treatment of actinomycetes with such mutagenic agents are known in the art and can be found by reference to *Manual of Industrial Microbiology and Biotechnology*, $2^{nd}$ edition (1999), (edited by Demain A. L. and Davies J. E.) (American Society of Microbiology, Washington, D.C.) at pages 353-361 and 717-724. In regards to the generation and selection of a mutant Actinomycete strain capable of overproducing a bioactive compound of interest, wherein the mutation event that results in the overproduction phenotype occurs as a naturally-occurring event (i.e a non-induced mutation), reference can be made to Shima et al. (1996) "Induction of Actinorhodin Production by rpsL (Encoding Ribosomal Protein S12) Mutations That confer Streptomycin Resistance in *Streptomyces lividans* and *Streptomyces coelicolor* A3(2)" *Journal of Bacteriology*, volume 178, pages 7276-7284, which describes a method of obtaining strains of *S. lividans* and *S. coelicolor* that produce elevated levels of the antibacterial compound actinorhodin by screening for naturally-occurring mutants that showed spontaneous resistance to the antibiotic streptomycin. Work performed subsequently by the Ochi et al. group (see Hesketh, A. and Ochi, K. (1997) "A Novel Method for Improving *Streptomyces coelicolor* A3(2) for Production of Actinorhodin by Introduction of rpsL (Encoding Ribosomal Protein S12) Mutations conferring Resistance to Streptomycin", *J. Antibiotics*, volume 50, pages 532-535)

disclosed a plausible link between the presence of a certain translation-associated mutations (alteration of the lysine amino acid residue at position 88 in the ribosomal protein S12), which can be selected for by screening for *Streptomyces* strains resistant to streptomycin, and the ability of the selected strains to biosynthesize larger amounts of actinorhodin. A combination of methods may also be employed to generate actinomycete strains capable of producing elevated levels of a bioactive compound of interest. In one embodiment, a *Micromonospora* strain of the present invention which is capable of producing an elevated level of the compound ECO-4601 in a fermentation culture was generated by exposing cells of a parent *Micromonospora* strain to concentrations of the antibiotic streptomycin wherein the ranges of concentrations used were greater than a minimal inhibitory concentration. An example of a minimal inhibitory concentration range of streptomycin is about 0.5 µg/mL to about 1.0 mg/mL. Preferably, a concentration range of streptomycin utilized to select for naturally-occurring resistance to the antibiotic is about 10 mg/ml to about 100 mg/ml. More preferably, the concentration of the antibiotic is one that achieves a kill rate of at least 95%, and most preferably the concentration of the antibiotic is one that achieves a kill rate of at least 99%. A bacterial colony that remains viable upon exposure to a level of streptomycin that provides a kill rate of at least 95% and more preferably a kill rate of at least 99% is subjected to a further mutagenesis treatment, for example, exposure to ultraviolet light. Levels of ultraviolet irradiation suitable for inducing mutations in Actinomycetes are known in the art (see above, *Manual of Industrial Microbiology and Biotechnology*), and in one embodiment of the present invention treatment of a *Micromonspora* strain selected for its resistance to high concentrations of streptomycin comprised exposure to ultraviolet irradiation at an exposure level of about 40 Joles/$m^2$ to about 45 Joles/$m^2$. In one embodiment of the present invention, such ultraviolet irradiation mutagenesis treatment results in a *Micromonospora* strain capable of an increased fermentation production of ECO-4601 of an at least five fold range when compared to the non-ultraviolet irradiated strain from which a five fold range level producing strain was derived.

ii) Recombinant Microorganisms

In another embodiment, the microorganism capable of producing the farnesylated dibenzodiazepinone ECO-4601 may be provided by recombining nucleic acid molecules that encode proteins useful in the production of farnesylated dibenzodiazepinones. Specifically, the microorganism capable of producing the farnesylated dibenzodiazepinone ECO-4601 may be provided by providing recombinant DNA vectors and nucleic acid molecules that encode all or part of the biosynthetic locus in strain 046-EC011, which directs the production of ECO-04601, and is referred to herein as "046D". Deposits of *E. coli* DH10B vectors, each harbouring a cosmid clone (designated as 046KM and 046KQ respectively) of a partial biosynthetic locus for the farnesyl dibenzodiazepinone from *Micromonospora* sp. strain 046-EC011 and together spanning the full biosynthetic locus for production of ECO-04601 have been deposited with the International Depositary Authority of Canada, Bureau of Microbiology, Health Canada, 1015 Arlington Street, Winnipeg, Manitoba, Canada R3E 3R2 on Feb. 25, 2003. The cosmid clone designated 046KM was assigned deposit accession numbers IDAC 250203-06, and the cosmid clone designated 046KQ was assigned deposit accession numbers IDAC 250203-07.

The deposit of the deposited *E. coli* DH10B vectors harbouring the cosmid clones has been made under the terms of the Budapest Treaty on the International Recognition of the Deposit of Micro-organisms for Purposes of Patent Procedure. The deposited clones will be irrevocably and without restriction or condition released to the public upon the issuance of a patent. The deposited clones are provided merely as convenience to those skilled in the art and are not an admission that a deposit is required for enablement, such as that required under 35 U.S.C. §112. A license may be required to make, use or sell the deposited strains, and compounds derived therefrom, and no such license is hereby granted.

Further, the present invention may be provided by further including one or more genetic modifications of 046D using conventional genetic recombinant techniques, such as mutagenesis, inactivation, or replacement of nucleic acids, to produce chemical variants of ECO-04601.

The farnesyl benzodiazepinone compound may be provided by a method wherein a transformed host cell comprising a recombinant DNA vector that encodes one or more of the polypeptides required for biosynthesis of ECO-4601, and culturing the host cell under conditions such that farnesyl benzodiazepinone is produced. In one embodiment, the host cell is a prokaryote. In another embodiment, the host cell is an Actinomycete. In another embodiment, the host cell is a *Streptomyces* host cell. In a further embodiment, the host cell is a non-Streptomycete Actinomycete such as a *Rhodococcus*, a *Mycobaterium*, or an *Amycolatopsis* species, or an non-Actinomycete bacterium such as a *Brevibacterium* or a species of *Myxococcus* such as *Myxococcus xanthus* (see Julien B. and Shah S. (2002) "Heterologous Expression of Epothilone Biosynthetic Genes in *Myxococcus xanthus*." *Antimicrobial Agents and Chemotherapy* 46: 2772-2778).

In a further embodiment, the present invention may be utilized in conjunction with recombinant nucleic acids that produce a variety of farnesyl dibenzodiazepinone compounds, or a dibenzodiazepinone bearing an acyl group other than a farnesyl moiety, that cannot be readily synthesized by chemical methodology alone. The invention allows direct manipulation of 046D biosynthetic locus via genetic engineering of the enzymes involved in the biosynthesis of a farnesyl dibenzodiazepinone, or an analog thereof, according to the invention.

Farnesyl dibenzodiazepinones and analogs can be produced by feeding one or more key intermediates or biosynthetic precursors (as defined in FIGS. 1-4) or close structural analogs, to a host cell comprising a recombinant DNA vector that encodes one or more of the polypeptides of the present invention, and culturing the host cell under conditions such that the farnesyl benzodiazepinone or analog is produced. Key intermediates are contacted directly with an isolated protein of the invention to perform the necessary steps for the production of a farnesyl dibenzodiazepinone (e.g., the farnesyl diphopshate and dibenzodiazepinone precursors can be coupled using an IPTN protein of the invention).

Key intermediates may be commercially available or may be prepared using standard chemical procedures or using the proteins of this invention. For example, farnesyl diphosphate and 3-hydroxyanthranilic acid are commercially available (e.g., Fluka F6892 and Aldrich 148776). 3-Amino-5-hydroxybenzoic acid, a precursor of the 2-amino-6-hydroxybenzoquinone, is prepared as described in Herlt et al (1981), *Aust. J. Chem.*, volume 34, pages 1319-1324.

iii) Recombinant DNA Vectors

Vectors that may be used in conjunction with the present invention typically comprise the DNA of a transmissible agent, into which foreign DNA is inserted. A common way to insert one segment of DNA into another segment of DNA involves the use of specific enzymes called restriction enzymes that cleave DNA at specific sites (specific groups of nucleotides) called restriction sites. A "cassette" refers to a DNA coding sequence or segment of DNA that encodes for an expression product that can be inserted into a vector at defined restriction sites. The cassette restriction sites are designed to ensure insertion of the cassette in the proper reading frame. Generally, a nucleic acid molecule that encodes a protein useful in the production of a farnesyl dibenzodiazepinone is inserted at one or more restriction sites of the vector DNA, and then is carried by the vector into a prokaryote e.g. Actinomycete, by transfection or transformation (see below). A segment or sequence of DNA having inserted or added DNA, such as an expression vector, can also be called a "DNA construct". A common type of vector is a "plasmid" which generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA. A suitable vector system may also comprise a Bacterial Artificial Chromosome (BAC) such as that described in Martinez et al. (2004), *Applied and Environmental Microbiology*, volume 70, pages 2452-2463. Coding DNA is a DNA sequence that encodes a particular amino acid sequence for a particular protein or enzyme. In one embodiment of the invention, the coding DNA encodes for polypeptides that may be useful for the biosynthesis of a farnesyl dibenzodiazepinone.

Promoter DNA of a recombinant vector is a DNA sequence that initiates, regulates, or otherwise mediates or controls the expression of the coding DNA. Promoter DNA and coding may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

Examples of promoters that function in actinomycetes, e.g. *Streptomyces*, are taught in U.S. Pat. Nos. 5,830,695 and 5,466,590. Another example of a transcription promoter useful in Actinomycetes expression vectors is tipA, a promoter inducible by the antibiotic thiostrepton [c.f. Murakami, T., et al., (1989), J. Bacteriol, 171, 1459].

iv) Transformation of Actinomycetes

A suitable transformation method for use with an actinomycete comprises forming the actinomycete culture into spheroplasts using lysozyme. A buffer solution containing recombinant DNA vectors and polyethylene glycol is then added, in order to introduce the vector into the host cells, by using either of the methods of Thompson or Keiser [c. f. Thompson, C. J., et al., (1982), J. Bacteriol., 151, 668-677 or Keiser, T. et al. (2000), "Practical *Streptomyces* Genetics", The John Innes Foundation, Norwich], for example. A thiostrepton-resistance gene is frequently used as a selective marker in the transformation plasmid [c.f. Hopwood, D. A., et al., (1987), "Methods in Enzymology" 153, 116, Academic Press, New York], but the present invention is not limited thereto. Additional methods for the transformation of actinomycetes are taught in U.S. Pat. No. 5,393,665, and see also Martinez et al. (2004) (supra) which teaches transformation of Actinomycetes by conjugation.

Protocols for the transformation of *Streptomyces* and non-Streptomycete Actinomycetes are known in the art [see, for example, Dijkhuizen, L. "Genetics of Non-*Streptomyces* Actinomycetes" in *Manual of Industrial Microbiology and Biotechnology*, 2 edition, A. L. Demain and J. E. Davies (ed.) [1999, ASM Press, Washington, D.C.] at pages 368-378; and also Nakashima N. et al. (2005) "Actinomycetes as host cell factories for production of recombinant proteins" *Microbial Cell Factories* 4:7]. Shuttle-vectors which may be used for the cloning one or more genes involved in a farnesylated dibenzodiazepinone biosynthetic pathway into a non-Streptomycete Actinomycete host. Such shuttle-vectors are made by recombining, through known molecular genetic techniques, genetic sequences from one or more non-Streptomycete, for example *Rhodococcus*, plasmids DNA into an *Escherichia coli* plasmid or derivative plasmid to generate a plasmid vector which is capable of replicating in both *E. coli* or *Rhodococcus* (while carrying the inserted gene(s) of interest). Such a host may include species of *Rhodococcous*, such as *Rhodococcus erythropolis, Rhodococcus equi* and *Rhodococcus globerulus*. Other non-*Streptomyces* Actinomycete that may be transformed, using a shuttle vector specific to the particular genus of bacteria, and used for heterologous expression of one or more genes involved in biosynthesis of the farnesylated dibenzodiazepinone include species of the *Mycobacterium* (for example, *Mycobacterium smegmatis*), and species of the genus *Amycolatopsis* (for example, *Amycolatopsis (Nocardia) lactamdurans* and *A. methanolica*), and species of the genus *Corynebacterium*. Heterologous expression of genes involved in biosynthesis of a secondary metabolite in a *Micromonospora* species has been successfully accomplished. For example, *Saccharopolyspora erythraea* (a megalomicin non-producer) was transformed with *Micromonospora megalomicea* genes encoding for production of megosamine. Culture of the transformed *S. erythraea* resulted in the production of meaglomicin by the transformed host cells (see, Volchegursky Y. et al. (2000) "Biosynthesis of the anti-parasitic agent megalomicin: transformation of erythromycin to megalomicin in *Saccharopolyspora erythaea*" Molecular Microbiology 37: 752-762).

Use of an Actinomycete for heterologous expression of a gene cluster that encodes for production of a microbial secondary metabolite that is used as an anti-tumor agent has been reported (see Sánchez C. et al. (2002) "The Biosynthetic Gene Cluster for the Antitumor Rebeccamycin: Characterization and Generation of Indolocarbazole Derivatives" *Chemistry & Biology* 9: 519-531; and Sanchez C. et al. (2005) "Combinatorial biosynthesis of antitumor indolocarbazole compounds" *Proc. Natl. Acad. Sci. (U.S.A.)* 102(2): 461-466). Furthermore, bacterial artificial chromosomes (BACs) for use in cloning very large fragments of DNA (up to 100 kilobases) for transformation into Actinomycetes are known in the art (see Sosio M. et al. (2000) "Artificial chromosomes for antibiotic-producing actinomycetes" *Nature Biotechnology* 18: 343-345), and which may be used to clone an entire gene cluster encoding for production of a microbial secondary metabolite or a natural bioanalog thereof.

v) Assay for Farnesyl Dibenzodiazepinone or Biosynthetic Intermediates

Actinomycetes defective in farnesyl dibenzodiazepinone biosynthesis may be transformed with one or more expression vectors encoding one or more proteins in the farnesyl benzodiazepinone biosynthetic pathway, thus restoring farnesyl benzodiazepinone biosynthesis by genetic complementation (in cis or in trans) of the specific defect.

The presence or absence of farnesyl dibenzodiazepinone or intermediates in the biosynthetic pathway (see FIGS. 1 to 4) in a recombinant actinomycete can be determined using methodologies that are well known to persons of skill in the art. For example, ethyl acetate extracts of fermentation media used for the culture of a recombinant actinomycete may be generated, for example as described in Example 1, and fractions therefrom containing farnesyl dibenzodiazepinone or intermediates detected by TLC on commercial Kieselgel 60F$_{254}$ plates. Farnesyl dibenzodiazepinone and intermediate compounds are visualized by inspection of dried plates under UV light or by spraying the plates with a spray containing vanillin (0.75%) and concentrated sulfuric acid (1.5%, v/v) in ethanol and subsequently heating the plate. The exact identity of the compounds separated by TLC is then determined using liquid chromatography-mass spectroscopy. Methods of mass spectroscopy are taught in the published U.S. Patent Application Publication No. US2003/0052268.

vi) Mutagenesis

In a further embodiment, a microorganism capable of producing a farnesylated dibenzodiazeonone or analogs thereof, and which may be used in conjunction with the present invention, may be provided for in part by direct manipulation of 046D biosynthetic locus via genetic engineering of the enzymes involved in the biosynthesis of the ECO-4601 farnesyl benzodiazepinone.

A number of methods are known in the art that permit the random as well as targeted mutation of the DNA sequences of the invention (see for example, Ausubel et. al. Short Protocols in Molecular Biology (1995) 3rd Ed. John Wiley & Sons, Inc.). In addition, there are a number of commercially available kits for site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

In addition, mutations in the nucleotide sequence of the 046D locus may be generated by insertional mutation or truncation (N-terminal, internal or C-terminal) according to methodology known to a person skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. Fourth, because of the non-template-dependent terminal extension activity of some thermostable polymerases, it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease Dpn I (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the isolation of mutant polynucleotides is described in detail as follows:

Plasmid template DNA (approximately 0.5 pmole) is added to a PCR cocktail containing: 1× mutagenesis buffer (20 mM Tris HCl, pH 7.5; 8 mM MgCl2; 40 µg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 µM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* cells according to standard methods.

Methods of random mutagenesis, which will result in a panel of mutants bearing one or more randomly situated mutations, exist in the art. Such a panel of mutants may then be screened for those exhibiting reduced uracil detection activity relative to the wild-type polymerase (e.g., by measuring the incorporation of 10 nmoles of dNTPs into polymeric form in 30 minutes in the presence of 200 µM dUTP and at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant polypeptides generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

B. Culture Medium and Facilities

Microorganisms capable of producing ECO-4601 are cultivated in a culture medium, preferably an aqueous culture medium, containing known nutritional sources for actinomycetes. Such culture medium comprise sources of carbon, nitrogen, various inorganic salts and other nutrients and growth factors that are assimable by actinomycetes. Preferred culture medium for fermentation of a microorganism capable of producing a farnesylated dibenzodiazepinone according to the present invention, preferably *Micromonospora* sp. [S01U02]046, include without limitation the culture medium listed in Table 1, and other suitable culture medium include, without limitation, the culture medium listed in Table 2. For fermentation processes that are to be conducted on a large-volume scale, preparation of an inoculum seed culture of a microorganism capable of producing a farnesylated dibenzodiazepinone according to the present invention, preferably *Micromonospora* sp. [S01U02]046, can be performed using culture medium KH, and culture medium HI can be used as the culture for the large volume fermentation. In another embodiment of the present invention, the seed medium is FBB (ingredient composition: potato dextrin (24 g/L), beef extract (3 g/L). Bacto-Casitone (5 g/L), glucose (5 g/L), yeast extract (5 g/L), and $CaCO_3$ (4 g/L, added after adjusting medium to pH 7.0)). In a still further embodiment of the present invention, medium HI may be used as the seed medium.

TABLE 1

Examples of Preferred Culture medium

| Component per Culture medium (g/L) | AP | CA | DZ | GP | HI | JA | MI | PI | QI | QP | YB |
|---|---|---|---|---|---|---|---|---|---|---|---|
| pH | 7 | 7 | 7 | * | 7 | 7.3 | 7 | 7 | 7 | 7.2 | 7 |
| Glucose | 60 | 10 | 5 | 30 | | | 10 | 10 | 10 | 12 | 20 |
| Cane molasses | | 15 | 10 | | | | | | | | |
| Soluble starch | | | 15 | 15 | | | 20 | | 25 | | |
| Corn starch | | | | | | 30 | | | | | |
| Potato dextrin | | 40 | | | 20 | | | 40 | | 10 | 50 |
| Corn steep liquor | | | | | | 15 | | | | 5 | |
| MOPS | 15 | | | | | | | | | | |
| Yeast extract | 8 | | | | 8.34 | | 5 | 5 | 5 | | 1 |
| Malt extract | 20 | | | | | 35 | | | | | |
| Pharmamedia | | | | 30 | | 15 | | | | 10 | 30 |
| Glycerol | | | | | 30 | | | | | | |
| N-Z Amine A | | 10 | | | | | | | | | |
| Proflo Oil ™ | | | | | | | | | | 4 | |
| Fish meal | | | 10 | | | | | | | | |
| Bacto-peptone | | | | | 2.5 | | 5 | 5 | 5 | | |
| $MgSO_4 \cdot 7H_2O$ | | 1 | | | | | | | | | |
| $CaCO_3$ | | 2 | 5 | 7 | 3 | 2 | 2 | 2 | 3 | | 5 |
| NaCl | 2 | | | | | | | | | | |
| $FeSO_4 \cdot 7H_2O$ | 0.01 | | | | | | | | | | |
| $MgSO_4$ | 0.1 | | | | | | | | | | |
| $ZnSO_4 \cdot 7H_2O$ | 0.01 | | | | | | | | | | |
| $CoCl_2 \cdot 2H_2O$ | | | | | | | | | | | 0.001 |

* pH not adjusted.

TABLE 2

Examples of Suitable Fermentation Media

| Component per Culture medium[1] (g/L) | AB | AC | CI | DA | FA | HA | KH | MA | MY | QB | RM | VA | VB | ZL |
|---|---|---|---|---|---|---|---|---|---|---|---|---|---|---|
| pH[2] | * | * | 7.0 | 7.0 | 7.0 | * | 7.0 | 7.5 | 7.0 | 7.2 | 6.85 | 7.0 | 7.0 | * |
| Glucose | | 5 | | 10 | 10 | 10 | 10 | | | 12 | 10 | 50 | 10 | 3 |
| Sucrose | | | | | 340 | | | | | | 100 | | 20 | |
| Maltose | | | | | | | | | 4 | | | | | |
| Cane molasses | | | | 10 | 15 | | | | | | | | 20 | |
| Corn starch | | | | | | | | | | | | | | |
| Soluble starch | 25 | 15 | | 5 | | | 25 | | 10 | | | | | |

TABLE 2-continued

Examples of Suitable Fermentation Media

| Component per Culture medium[1] (g/L) | AB | AC | CI | DA | FA | HA | KH | MA | MY | QB | RM | VA | VB | ZL |
|---|---|---|---|---|---|---|---|---|---|---|---|---|---|---|
| Potato dextrin | | | 20 | 20 | 40 | | 20 | | | | | | 10 | |
| Corn steep solid | | | | 5 | | | | | | | | | | |
| Corn steep liquor | | 10 | | | | | | | | 5 | | | | |
| Corn meal | | | | | | | | | | | | | | 10 |
| Corn starch | | | | | | | | | | | | | | |
| Soybean flour | | | | 5 | | | | | | | | 30 | | |
| Soybean powder | | | | | | | | 15 | | | | | | |
| Dried yeast | | | | | | | | | 2 | | | | | |
| Torula yeast | | | | | | | | | | | | | | 4 |
| Yeast extract | | | | | 3 | 5 | | | 4 | | 5 | | | |
| Malt extract | | | | | 3 | | | | 10 | | | | | |
| Pharmamedia | | | | | | | | | | 10 | | | | |
| Glycerol | 25 | | 20 | 10 | | | | | | | | | | |
| Mannitol | 25 | | | | | | | | | | | | | |
| N-Z Amine A | | | | | 10 | | 5 | | | | | | | |
| L-Glutamine | 5.84 | | | | | | | | | | | | | |
| L-Arginine | 1.46 | | | | | | | | | | | | | |
| Soybean powder | | | | | | | | | | | | | | |
| Fish meal | | | 10 | | | 5 | | | | | | | | 10 |
| Bacto-peptone | | | 5 | | | | | | | | | | | |
| Soytone-peptone | | | | | | | | | | | | | 5 | |
| KH$_2$PO$_4$ | 1 | | | | | | | | | | | | | |
| MgSO$_4$·7H$_2$O | 0.5 | | | 0.5 | 1 | | | | | | | | | 1 |
| CaCO$_3$ | | 4 | 2 | 3 | 2 | | 1 | 4 | | | 6 | | 2.5 | 5 |
| NaCl | 1 | 5 | | | | | | | 5 | | 5 | | | |
| MnCl$_2$·4H$_2$O | | | | 0.1 | | | | | | | | | | |
| ZnCl$_2$ | | | | 0.1 | | | | | | | | | | |
| FeCl$_2$·4H$_2$O | | | | 0.1 | | | | | | | | | | |
| (NH$_4$)$_2$SO$_4$ | | 3.5 | 2 | | | | | 2 | | | 3 | | | |
| K$_2$SO$_4$ | | | | | | | | | | | 0.25 | | | |
| MgCl$_2$·6H$_2$O | | | | | | 1 | | | | | 10.128 | | | |
| Na$_2$HPO$_4$ | | | | | 3 | | | | | | | | 2 | |
| KCl | | | | | | | | | | | | | | 2 |
| Phytic acid | | | | 1 | | | | | | | | | | |
| Sodium citrate | | | | | | | | | | | | | 2.5 | |
| Casamino acid | | | | | | | | | | | 0.1 | | | |
| Proflo oil ™ (mL/L) | | | | | | | | | | 4 | | | | |
| MOPS | | | | | | | | | | | 21 | | | |
| Trace element solution #1[3] (mL/L) | 2 | | | | | | | | | | | | | |
| Trace element solution #2[4] (mL/L) | | | | | | | | | | | 1 | | | |

[1]Media components are described in g/L, unless otherwise noted.
[2]The pH is adjusted as indicated prior to the addition of CaCO$_3$. The symbol * indicates no adjustment of pH.
[3] Trace element solution #1 contains (per 100 mL of solution, made in deionized, distilled (dd) H$_2$O): ZnSO$_4$·7H$_2$O (10 mg), FeSO$_4$·7H$_2$O (100 mg), CuSO$_4$·5H$_2$O (10 mg), MnSO$_4$·H$_2$O (10 mg), Na$_2$B$_4$O$_7$·10H$_2$O (10 mg), (NH$_4$)$_6$Mo$_7$O$_{24}$·4H$_2$O (10 mg).
[4]Trace element solution #2 contains (per 1000 mL of solution, made in deionized, distilled (dd) H$_2$O): ZnCl$_2$ (40 mg), FeCl$_2$·6H$_2$O (200 mg), CuCl$_2$·2H$_2$O (10 mg), MnCl$_2$·4H$_2$O (10 mg), Na$_2$B$_4$O$_7$·10H$_2$O (10 mg), (NH$_4$)$_6$Mo$_7$O$_{24}$·4H$_2$O (10 mg).

Fermentation procedures for culturing a microorganism capable of producing a farnesylated dibenzodiazepinone according to the present invention follow equipment sterilization and safety practices and techniques to allow for aseptic growth conditions pertaining to the culturing of microorganisms as practiced by those of skill in the art (see generally, *Manual of Industrial Microbiology and Biotechnology*, supra).

Suitable containers for fermentation of a culture medium inoculated with a microorganism capable of producing a farnesylated dibenzodiazepinone according to the present invention are known in the art and can be selected depending on a volume of fermentation broth that is desired to be produced. Containers for fermentation at a laboratory-scale level of production may comprise, for example, the use of a sterile, foam-stoppered 2 liter, baffled Erlenmeyer type flask, containing about 500 mL of culture medium and inoculated with a microorganism capable of producing a farnesylated dibenzodiazepinone. Containers containing inoculated culture medium can be agitated, for example by shaking on a rotary shaker or in a heated water bath at a rotation speed of about 250 revolutions per minute, to maintain a level of dissolved oxygen in the media sufficient for the growth of the inoculated microorganism. Aeration may also be accomplished by injection of air, oxygen or an appropriate gaseous mixture into the culture medium during incubation. A suitable fermentation temperature range and time to produce a fermentation broth comprising the farnesylated dibenzodiazepinone, at such laboratory-scale level, are about 27° C. to about 29° C., and 72 hours to about 100 hours, respectively. Suitable incubation conditions also comprise maintenance of the fermentation broth at a pH range of about 6 to about 9, and more preferably a pH range of about 7 to about 8, during the incubation period.

In a research laboratory setting, an automated benchtop fermentor may be utilized to produce a quantity of a fermentation broth comprising the farnesylated dibenzodiazepinone. Such fermentors are known to those of skill in the art and are available from a number of commercial suppliers, for example New Brunswick Scientific Inc. or Sartorius AG. Such fermentors may provide a range of fermentation volumes, for example from about 1 liter to about 20 liters, with a working volume in a range of less than one liter to about 15 liters. Preferably, such a fermentor is equipped with systems and accessories for control and monitoring of fermentation conditions, for example: a heat-blanketed or water-jacketed stainless steel or glass fermentation vessel or a vessel having an immersed heating/cooling coil; a mechanically-sealed stirring shaft fitted with one or more suitable impellers (for example, Rushton-type impellers) and which can be operated at variable rotational speeds suitable to achieve proper agitation of the fermentation broth; one or more peristaltic pumps for the addition or removal of liquids; one or more probes to automate and monitor liquid additions/removals and control of foaming of the fermentation broth; probes and controls for monitoring and adjusting of the fermentation broth pH and dissolved oxygen content; solenoid valves to allow for a sequential addition of desired gases to the fermentation broth; and an electronic control unit equipped (which may include a visual display system) with appropriate software for programming and monitoring of the fermentation conditions and which may provide an electronic and/or printed record of the fermentation. In a preferred embodiment of the present invention, a New Brunswick Scientific Inc. BioFlo® 110 fermentor is used for fermenting a strain of a microorganism capable of producing ECO-4601.

In a further embodiment of the present invention, fermentation of a strain of a microorganism capable of producing ECO-4601 can occur using a large volume fermentor, more preferably using one or more pilot plant scale fermentation vessels. Pilot plant scale vessels, as recognized by those of skill in the art, may range in size of their volumetric capacity from about 20 liters to about 7,500 liters, more preferably from about 75 liters to about 3,000 liter vessels, and even more preferably from about 100 liter to about 2,000 liter vessels. Numerous manufacturers and suppliers of large-scale fermentation vessels and accessory systems are available for those of skill in the art. Such suppliers and manufacturers may include, but are not limited to, New Brunswick Scientific Co. (Edison, N.J.), Chemap AG (Volketswil, Switzerland), Applikon Inc. (Schiedam, The Netherlands), Sartorius BBI Systems, Inc. (Bethlehem, Pa.), Marubishi Laboratory Equipment Co., Ltd. (Japan), and L.H. Engineering Co. (United Kingdom). As noted by Hosobuchi M. and Yoshikawa "Scale-Up of Microbial Processes" (in *Manual of Industrial Microbiology and Biotechnology*, $2^{nd}$ edition (1999), (edited by Demain A. L. and Davies J. E.) (American Society of Microbiology, Washington, D.C.) at pages 353-361) and by Junker B. in "Multipurpose Fermentor Design: Critical Considerations" *Chemical Engineering* February 2003 at pages 1-6, a number of factors may require adjustment in order to optimize conditions for large-scale fermentation production depending upon the size and type of fermentation vessel selected for use. Such factors may include, for example, those of a mechanical/physical nature such as the type and number of impellers and baffles, the agitation speed and power per unit volume, the impeller tip speed (which may influence shear stress inflicted upon the microorganisms), and the aeration rate and pressure. As will be appreciated by those of skill in the art, depending upon the capacity of the large volume fermentation vessel that is to be used, inoculation of the culture medium in the selected large volume fermentation vessel may require as fermentation production of one or more seed cultures of the microorganism capable of producing the farnesylated dibenzodiazepinone which are subsequently utilized for production of a quantity of inoculum sufficient for inoculation of the culture medium in the large volume fermentation vessel. Seed cultures may be prepared, for example, in one or more baffled seed flasks maintained as per conditions for fermentation production at a laboratory-scale level of production, and one or more aliquots from such seed cultures may be withdrawn during to access purity and viability of the culture prior to inoculation of the inoculum fermentor. Production of a volume of inoculum fermentation broth should be commensurate with the volume of culture medium to be inoculated in the large fermentation vessel. Preferred volume range of an inoculum fermentation broth for use in accordance with the present invention is about 2% to about 10% of the volume of the volume of culture medium contained in the large volume fermentation vessel, and more preferably about 3% to about 4% of the volume of the culture medium contained in the large volume fermentation vessel, and most preferably about 3.2% to about 3.5% of the volume of the culture medium contained in the large volume fermentation vessel. In accordance with the present invention, a Chemap AG type M16K inoculum fermentor may be used for producing an inoculum culture that can be used to inoculate a volume of culture medium contained in a large volume fermentor. A Chemap AG type CF/569 having a total capacity of 750 liters with impellers mounted on a drive (as measured from the bottom of the vessel) and situated at a about a 70 liter mark, and at about a 200 liter mark, and at about a 340 liter mark may be used in accordance with the present invention.

It will be recognized by those of skill in the art that the first concentrate comprising the farnesylated dibenzodiazepinone of Formula I obtained by the method of the present invention may be processed downstream of the production of the first concentrate so as to reduce a level of an impurity in the first concentrate. Such processing may occur in any one of a number of manners as recognized by those of skill in the art, for example, by employing a column cleanup process to reduce a level of an impurity, as exemplified in one or more of the examples below which are not to be considered as to be limiting as to a particular method that may be selected so effect such downstream processing.

EXAMPLES

Unless otherwise indicated, reagents and solvents used in the following examples were supplied by Sigma-Aldrich and or Fisher Scientific. Unless otherwise indicated, all numbers expressing quantities of ingredients and properties used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting.

Example 1

Production of *Micromonospora* Sp. Strain [S01U02]

1.1 First Round of Strain Improvement

*Micromonospora* sp. strain 046 (accession number IDAC 070303-01) was streaked on culture plates bearing GYM agar medium containing 10-100 μg/mL streptomycin. The ingredients for GYM agar medium comprised (in g/L): glucose (4 g), yeast extract (4 g), malt extract (10 g), N-Z Amine A (1 g), NaCl (2 g), agar (20 g), made to 1000 mL with distilled water, pH 7.2 (see Shima J. et al. (1996) "Induction of Actinorhodin Production by rpsL (Encoding Ribosomal Protein S12) Mutations that Confer Resistance in *Streptomyces lividans* and *Streptomyces coelicolor* A3(2)" J. Bacteriol., vol. 178 (24), pages 7276-7284). Inoculated plates were incubated at 28° C. for 4 to 10 days. Single colonies exhibiting natural resistance to the antibiotic were obtained, and were thereafter streaked onto GYM agar media plates containing a similar concentration of streptomycin as the plate from which the particular colony was selected. The plates were incubated at 28° C. for 15 to 20 days. Surface growth from each plate was used to inoculate (for each plate) one glass culture tube (150 mm×20 mm) containing 5 mL medium KH (no streptomycin was added to the seed medium). Inoculated culture tubes were incubated at 28° C. for a period of 70-72 h on a rotary shaker operating at 250 RPM to allow for bacterial cultures to grow. After the cultivation period, a 0.250 mL aliquot was taken form each culture tube (seed culture) and was transferred into similar tubes containing 10 mL culture medium C1.

Inoculated culture tubes were incubated at 28° C. for a period of 7 days on a rotary shaker operating at 250 RPM to allow for bacterial cultures to grow and produce ECO-4601. After completion of the fermentation, 10 mL of ethyl acetate was added to each tube, and the tubes were returned to the shakers for agitation for 20 min. The content of each tube was transferred into separate 45 mL Falcon tubes and centrifuged at 4500 RPM for 10 min to generate an upper organic phase and a lower aqueous phase within the tube. A 5 mL aliquot of the organic phase (upper phase) was taken from each tube and transferred into separate small glass tubes (100×13 mm), and the solvent was evaporated under nitrogen stream to give a dried residue within each tube. The dried residue was re-dissolved in 0.5 mL methanol and assayed by LCMS for ECO-4601 content. Approximately 850 single colonies were screened as such, from which a single colony (clone) was identified that produced ECO-4601 at a yield of approximately 10-25 mg/L, such yield being approximately 10 fold higher than that produced by controls (equivalent liquid cultures of the parent strain). The selected clone was resistant to the highest concentration of streptomycin (100 μg/mL), and was designated *Micromonospora* sp. strain [S01]046 (accession number IDAC 231203-01).

1.2 Second Round of Strain Improvement

In a second round of strain improvement, *Micromonospora* sp. strain [S01]046 was streaked on culture plates bearing GYM agar medium. The plates were incubated at 28° C. for 15-20 days until abundant sporulation occurred. Spores were collected from each plate by flooding the plate with 5 mL of sterile distilled water, scraping off the spores from the entire plate and pipetting the suspended spores into a 15 mL conical tube that was then centrifuged at 5000 RPM for 10 minutes at 4° C. The supernatant was discarded by pipetting off from the centrifuged tube, and the spore pellet resuspended in 10 mL of sterile distilled water and thoroughly vortexed. Agar pieces, if present, were removed from the spore resuspension by filtering the resuspension through cotton placed in a syringe followed by re-centrifugation at 5000 RPM for 10 minutes at room temperature, followed by decanting of the supernatant by pipetting-off. Centrifuged spores resuspended with sterile distilled water and diluted (with sterile distilled water) to reach a level of 8000 to 20000 spores/m L.

From the diluted spore suspension (whether cotton-filtered or not), a 0.5 mL aliquot was taken and drops were evenly spread onto the agar surface of GYM agar plates. Plates were allowed to dry in laminar flow under aseptic conditions for 10 minutes, while the lid of each played was kept ajar during the drying period. The plated spores were then subjected to ultraviolet (UV) irradiation at intensities of 40-45 Joles/m$^2$ of the agar surface. The lids were removed from the plates during the UV treatment. To prevent reversal, by light energy, of mutations induced by the UV treatment, plates that were subjected to the UV treatment were thereafter maintained in a light-proof container at 28° C. for at least 24 hours. The irradiated plates were thereafter incubated at 28° C. for 4 to 10 days or until single colonies appeared. Surviving colonies (approximately 0.1%) were picked, streaked onto GYM agar media plates and incubated at 28° C. for 15 to 20 days or until abundant sporulation occurred.

Clones from the surviving colonies were screened for production of ECO-4601 as described above for first round screening to obtain antibiotic resistant clones. Non-UV treated cultures of strain [S01]046 were grown under similar conditions and used as control. From this second round of screening, a single strain was identified to produce ECO-4601 at 4-6 fold higher than the control strain. This new strain was designated *Micromonospora* sp. strain [S01U02]046 (deposit accession number IDAC 070905-01). When grown in 14-L fermentors containing 10 L of culture medium HI (Table 1), strain [S01U02]046 was found to produce ECO-4601 at a yield rate of approximately 172±24 mg/L.

Example 2

Small-Scale Laboratory Production

To assess whether a variation in the fermentation conditions may result in an increase in yield of ECO-4601 in the fermentation broth, a small-scale fermentation and extraction procedure was adopted as follows.

2.1 Preparation of Flasks

Three glass beads (5 mm diameter) were placed in each of two, 125 mL Erlenmeyer flasks and the flasks are autoclaved. A volume of 25 mL of sterilized HI media was then aseptically transferred into each flask. Thereafter, an aliquot of conditioned, sterile HP20 resin suspension was added to each flask to give a 1% HP20 resin content per flask (1 mL from a 0.25 g/mL sterile stock solution). Preparation of the HP20 resin suspension consisted of measuring an amount of dry HP20 into a beaker and adding a volume of 100% methanol sufficient to cover the dry resin. The contents of the beaker were then thoroughly mixed to evacuate any air bubbles from the resin, and the HP20 resin was allowed to settle in the beaker. After settling, the methanol was decanted, and the methanol treatment step repeated once. The methanol-conditioned HP20 resin was then washed 5 times with distilled water, and after the fifth wash, sufficient water was added to the sterile conditioned HP20 resin to give a stock solution having a concentration of 0.25 g/mL, and the prepared flask sterilized in an autoclave (121° C.) for 30 min.

2.2 Preparation of Seed Culture

A seed culture of *Micromonospora* sp. strain [S01U02]046 was prepared by transferring the contents of two glycerol stock vials (each vial was maintained at −80° C. until use and contained 1.5 mL of frozen bacterial culture) into one, 2-L baffled flask containing 500 mL of aqueous culture medium KH. The seed culture was grown at 28° C. for 3 days with shaking at 250 RPM.

To produce the glycerol stock tubes, surface growth from a sporulated GYM plate of [S01U02]046 that was incubated at 28° C. for 17 to 20 days was transferred into three, 2-L baffled flasks each containing 500 mL of KH medium. The cultures were then grown at 28° C. for 3 days with agitation at 250 RPM. A pooled culture was prepared by mixing 100 mL from each flask in a separate sterile flask (300 mL total) under aseptic conditions. An equal volume from a sterile 40% (v/V) glycerol-in-water solution was added to the pooled culture, mixed and dispensed in 1.5 mL aliquots in 2 mL screw cap tubes and stored at −80° C.

2.3 Inoculation of Production Culture Medium

For each experiment, duplicate Erlenmeyer flasks were prepared as per Section 2.1, and each flask was inoculated with a 0.5 mL (2% V/V) aliquot of the seed culture grown as described above at 250 RPM. Inoculated flasks are placed in a rotary shaker that is operated at 250 RPM and cultures are grown at 28° C. for a period of 4 days.

2.4 Extraction

On the fourth day (96 hrs) of fermentation culturing, a 2 mL aliquot of the fermentation broth was removed from each flask and transferred into a 15 mL screw cap tube to which 2 mL of ethyl acetate was added. The tube was then vortexed at high speed for approximately 2 minutes, and then centrifuged (Sorval Legend™ RT) for 10 minutes at 5350 RPM at room temperature to generate an upper organic phase and a lower aqueous phase (containing bacterial mycelia and the HP20 resin) within the tube. A 0.5 mL aliquot of the upper was removed and transferred to a borosilicate glass tube (13×100 mm) and the contents of the glass tube dried under nitrogen at 40° C. for 10 minutes. The resulting dried residue was resuspended in 0.5 mL of 100% methanol (with brief vortexing to ensure complete resuspension). A 150 µL aliquot of the residue resuspension was taken for analysis of ECO-4601 content.

2.4 Results

Results from replicate experiments to assess whether the presence of an amount of methanol-conditioned HP20 resin in the fermentation culture broth during fermentation period resulted in an increased production of ECO-4601 are shown in Table 3 directly below.

TABLE 3

Small-scale fermentation broth concentrations of ECO-4601

| | ECO-4601 CONTENT (mg/mL of fermentation broth, based on analysis of extracts of the fermentation broth at 96 hrs) | | | |
|---|---|---|---|---|
| | Experiment 1 | | Experiment 2 | |
| CONDITION | Flask 1 | Flask 2 | Flask 1 | Flask 2 |
| HI culture medium | 7.00 | 7.30 | 7.36 | 7.21 |
| HI culture medium + HP20 (1% in media) | 329 | 302 | 263 | 265 |

The above-noted results indicated that the presence of resin in the fermentation broth could correlate with an increase in production of ECO-4601 and thereby result in an increased ECO-4601 yield.

Example 3

Small Scale Laboratory Production

A small-scale fermentation culture was grown and extracted as described above in Example 2 with the exception that triplicate flasks were grown for a single experiment. The results from the triplicate flasks are shown below in Table 4.

TABLE 4

Small-scale fermentation broth concentrations of ECO-4601

| | ECO-4601 CONTENT (mg/L of fermentation broth, based on analysis of extracts of the fermentation broth at 96 hrs) | | |
|---|---|---|---|
| | Experiment 1 | | |
| CONDITION | Flask 1 | Flask 2 | Flask 3 |
| HI culture medium | 7 | 7.33 | 8.01 |
| HI culture medium + HP20 (1% in media) | 465 | 310 | 380 |

The above-noted results further indicated that the presence of resin in the fermentation broth could correlate with an increase in production of ECO-4601 and thereby result in an increased ECO-4601 yield.

Example 4

Scale-Up Production—Benchtop Fermentation Batch Cultures 4.1 Inoculum Production and Benchtop Fermentation

*Micromonospora* sp. strain [S01U02] (deposit accession number IDAC 070905-01) was maintained on agar plates of GYM agar. An inoculum for the benchtop fermentation was prepared by transferring the surface growth of the *Micromonospora* sp. from the agar plates to 2-L flasks containing 500 mL of sterile KH medium. Each liter of KH medium comprises 10 g glucose, 20 g potato dextrin, 5 g yeast extract, 5 g NZ-Amine A, and 1 g $CaCO_3$ made up to one liter with water (pH 7.0). The inoculum culture was incubated at about 28° C. for approximately 70 hours on a rotary shaker set at 250 rpm. Following incubation, 300 mL of culture was transferred to a 14.5 L BioFlo® 110 fermentor (New Brunswick Scientific, Edison, N.J.) containing 10 L of sterile production culture medium HI. Each liter of production medium HI was composed of 20 g potato dextrin, 30 g glycerol, 2.5 g Bacto-peptone, 8.34 g yeast extract, and 3 g $CaCO_3$, (added after pH adjustment) (with 0.3 mL Silicone defoamer oil (Chem Service) and 0.05 ml Proflo Oil™ (Traders protein) as antifoam agents). Media contents were mixed into 3 L of distilled water for approximately 30 minutes using a magnetic stirrer operating at a medium speed, and the contents adjusted to pH 7.0 followed by the addition of the $CaCO_3$, Proflo™ oil and Silicon defoamer. The vessel was sterilized at 121° C. for 40 min. Cultures were grown by fermentation for 96±4 hr at 28° C., with dissolved oxygen (DO) controlled at 25% in a cascade loop with agitation varied between 350-650 RPM and aeration set at a fixed rate of 0.5 V/V/M.

To assay for the amount of ECO-4601 present in the fermentation broth at the time of completion of fermentation period, a 5 mL aliquot of the fermentation broth was also removed (in-process fermentation sampling and extractions were also performed on the morning and evening of days 2 and 3 for each fermentation culture). The 5 mL aliquot was subjected to the ethyl acetate extraction procedure as generally described above in Example 2, section 2.3, with the exception that the 5 mL aliquot of the fermentation broth was extracted with 5 mL of ethyl acetate in a 50 mL screw cap tube, and that the dried residue was resuspended in 1 mL of 100% methanol. The methanol-resuspended residue was thus diluted by a factor of 2× for assay by HPLC/UV to determine the production yield (concentration expressed as mg/L) of ECO-4601 in the fermentation broth. HPLC/UV assays were performed using either a Waters Alliance 2690 Separations Module (Waters Corp., Milford, Mass.) equipped with a Waters PDA 996 detector, or a Waters Alliance 2695 Separations Module equipped with a Waters Dual Wavelength 2487 detector. HPLC columns used were selected from either an ACE 3 AQ C18, 3.0×100 mm+3.0×10 mm guard 3 u (Canadian Life Sciences, Inc., Peterborough, Ontario, Canada) or a Symmetry C18, 4.6×150 mm+3.0×20 mm guard 5 u (Water Corp.). For both column types, the solvents used were: Solvent A—$H_2O$+0.4% formic acid (996:4 mL); Solvent B—Acetonitrile+0.4% formic acid (996:4 mL). The flowrate and time for the ACE column was set to 1.00 mL/min and 16 minutes, while the flow rate for the Symmetry column was set 1.30 mL/min and 15 minutes. For both column types, a 20 uL sample was injected at room temperature, with pressure set at a minimum of 20 bar and a maximum of 300 bar, with detection occurring at 294. Optionally, detection could have been performed at 230 nm.

A number of separate fermentation broth cultures were grown as described above. As noted above, in-process samples aliquots were taken from each fermentation broth on the morning and evening of the second day of fermentation; on the morning, afternoon and evening of the third day of fermentation; and on the morning of the fourth day of fermentation. For each fermentation culture, a yield rate (that being a rate of production of ECO-4601 in terms of mg of ECO-4601 per liter of broth per hour) could be assessed given an overall time period for each fermentation culture and mass of ECO-4601 present in the fermentation broth at the time of completion of the fermentation. Also, it was observed that for each fermentation culture the rate of production of ECO-4601 varied over a range of values throughout the course of the fermentation culture time period, but increased more steeply between the second and third day of fermentation culturing. Values for the yield rate for the series of fermentation cultures noted directly, calculated on the basis of in-process sample aliquots taken on the afternoon of the second day and the morning of the third day of fermentation are presented in Table 5, noted directly below.

TABLE 5

In-process Fermentation Culture Analyses

| | BioFlo 110 Fermentation Broth Batch No. | | | | | | | |
|---|---|---|---|---|---|---|---|---|
| | 135 | 136 | 137 | 138 | 139 | 140 | 141 | 142 |
| Day 2 PM [ECO-4601 mg/L] | 24.16 | 7.26 | 30.6 | 28 | 54.6 | 18.05 | 14.06 | 11.21 |
| Day 3 AM [ECO-4601 mg/L] | 93.49 | 60.24 | 128.4 | 126.8 | 130 | 73.63 | 64.77 | 47.72 |
| Number of Hours b/n D2-PM & D3-AM Samples | 17 | 17 | 19.5 | 19.5 | 19.5 | 17 | 17 | 17 |
| Difference in [ECO-4601] b/n D2-PM & D3-AM | 69.33 | 52.98 | 97.8 | 98.8 | 75.4 | 55.58 | 50.71 | 36.51 |
| Yield Rate (mg/L/hr) | 4.08 | 3.12 | 5.01 | 5.06 | 3.87 | 3.27 | 2.95 | 2.15 |

Results shown in Table 5 indicated that while the yield rate can vary between fermentation batches, a yield rate of over 5 mg/L/h was achieved.

Presented below in Table 6, from each of the separate fermentation broth cultures grown as described above, are the data which showed ECO-4601 fermentation broth concentration and mass per fermentation broth culture at the time of completion of each fermentation broth culture's incubation period.

TABLE 6

Fermentation broth concentrations of ECO-4601 (on completion of fermentation)

| | BioFlo 110 Fermentation Broth Batch No. | | | | | | | |
|---|---|---|---|---|---|---|---|---|
| | 135 | 136 | 137 | 138 | 139 | 140 | 141 | 142 |
| Broth concentration of ECO-4601 (mg/L) | 97.56 | 88.71 | 122 | 137.6 | 130.4 | 108.87 | 54.49 | 115.08 |
| Mass (mg) of ECO-4601 in Broth | 878 | 798.4 | 1098 | 1238.4 | 1173.6 | 1088.7 | 517.7 | 1093.3 |

4.2 Harvesting, Extraction and Concentration

For each fermentation batch culture, after removal of the assay aliquot from the fermentation broth, the pH of the fermentation broth was adjusted to 3.0±0.2 by the drop-wise addition of 20% aqueous $H_2SO_4$ (sulfuric acid) and with constant stirring.

The resulting acidified mixture was further treated by being cooled to 4° C. and incubated at that temperature for a period of 12 h to 48 h (maximum 72 hours). Batches were combined into larger holding flasks or carboys (10 L or 20 L volume, as required) for the period at which they were held at 4° C. On completion of the 4° C. incubation period, the cold fermentation broth was aliquoted into 750 mL polypropylene centrifuge tubes and centrifuged (Sorval RT-7) at 3000-3500 rpm for 15-20 min. The supernatant was discarded and the mycelial pellets were combined to give a total combined pellet mass of 1400 grams. The combined mycelial pellet was then extracted three times (90 minutes, 90 minutes, 30 minutes, with stirring at medium to high speed) with 100% methanol (HPLC grade, J. T. Baker), using a methanol volume per extraction round of 300±5 mL for every 100 g of mycelia. The methanol extracts (three rounds) were pooled and filtered through Whatman #4 filter paper.

The filtered extract was treated, as follows, to form a first concentrate: 330 g of HP20 resin was loaded into a 10 L rotary evaporator flask, which was then mounted onto a rotary evaporator system (Buchi Rotavapor® (Model R-200) equipped with a Buchi heating bath (Model B-490) set to 40° C., and a Buchi vacuum pump (Model V-500)). Aliquots of the filtered extract were introduced into the evaporator flask over the course of an evaporation process that lasted 22±2 hours evaporation. On completion of the evaporation process, a volume of 2200 mL of residual water remained in the evaporation flask together with the HP20 onto which the ECO-4601 was adsorbed. HPLC-UV analysis of the residual water indicated that 69 mg of ECO-4601 remained in the residual water (31.36 mg/L), thereby indicating that over 99% of the ECO-4601 from the filtered extract was adsorbed onto the HP20 resin.

Example 5

Scale-Up Production—Benchtop Fermentation Batch Cultures

In a further example of a benchtop fermentation, fermentation cultures were generated, as described in Example 4, using the BioFlo® 110 fermentor. Aliquots from each fermentation batch were taken upon the completion of the fermentation period for each batch and analyzed by HPLC-UV as described in Example 4 to establish the ECO-4601 concentration, and thereby the mass of ECO-4601, in each fermentation batch culture at the time of the fermentation period's completion per culture. Results from such analyses are shown below in Table 7.

TABLE 7

Fermentation broth concentrations of ECO-4601 (on completion of fermentation)

| | BioFlo 110 Fermentation Broth Batch No. | | | | | | | |
|---|---|---|---|---|---|---|---|---|
| | 4001 x02 | 4001 x03 | 4002 | 105 | 106 | 107 | 108 | 109 |
| Concentration of ECO-4601 (mg/L) | 101.56 | 139 | 90.43 | 152 | 91 | 117 | 157 | 122 |
| ECO-4601 mass (mg) in Broth | 810.24 | 1320.5 | 723.44 | 1216 | 864.5 | 1111.5 | 1491.5 | 1159 |

Upon completion of the fermentation period, the fermentation cultures were acidified, combined (total volume of the combined fermentation broths being about 71.5 L) and cooled as described above prior to harvesting of the particulate matter (mycelia) from the combined fermentation broths by centrifugation. Harvested mycelia were subjected to 3 rounds of methanol extraction as described in Example 4. HPLC-UV analysis of the methanol extract indicated an extracted mass of ECO-4601 of 7470 mg.

Example 6

Figure 5:
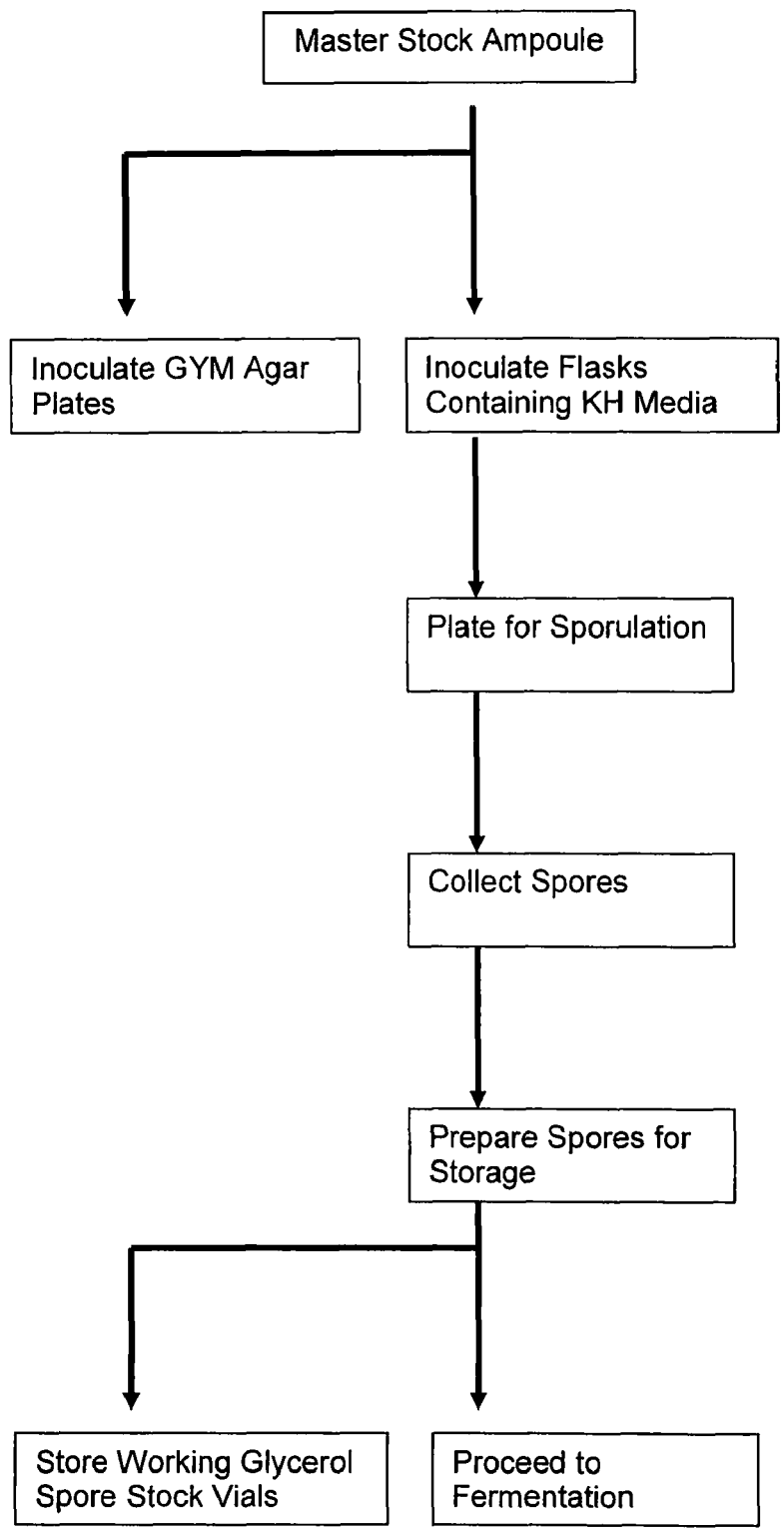
FIG. 5 is a flowchart depicting a plurality of steps involved in a procedure for the preparation of master and working seed stocks for use in a pilot fermentation production.

Scale-up Production—Large Volume/Pilot Plant Fermentation 6.1. Preparation of a Master Seed Stock Pilot manufacturing master seed stocks were prepared as generally illustrated in FIG. 5. A spore pellet was obtained from a lyophilized master vial of *Micromonospora* sp. [S01U02]046, and was aseptically transferred into a sterile, 50 mL tube to which 2.5 mL of TSB-medium (Trypticase Soy Broth, from Becton Dickson) had been added. The tube was then vortexed to obtain a homogeneous suspension of the lyophilized spore pellet. Two 0.5 mL aliquots of the pellet suspension were withdrawn from the tube and spread evenly on separate GYM agar control plates (GYM agar medium (per 1000 mL): glucose (4 g); yeast extract (4 g); malt extract (10 g); NZ-Amine A (1 g); NaCl (2 g); agar (20 g), pH 7.2) to assess for purity and growth of the bacteria. Inoculated GYM plates were incubated for at 28±1° C. for about 72 hours. Concomitant with the inoculation of the GYM control plates, a 0.5 mL aliquot of the pellet suspension was inoculated into each of two 125 mL flasks each containing 25 mL of KH media and three glass beads (5 mm diameter). Inoculated flasks were incubated at 28±1° C. for about 72 hours to about 96 hours in a rotary shaker operating at 250-300 RPM (until orange mycelia appeared in the culture medium). Aliquots from the 125 mL flasks were then plated on GYM agar plates and incubated for 17.5±2.5 days to obtain dark spores at the mycelial surface. Spores were collected (in a laminar flow hood) by flooding each plate with about 5 mL of sterile distilled water and scraping with a sterile bacteriological loop, flowed by transfer of the resuspended spores into a 50 mL conical tube via filtering through cotton plugs. The spore suspension was then centrifuged (5,000 RPM, 10 minutes at 4° C.) to obtain a spore pellet, which was subsequently washed (vortexed) with 10 mL of sterile water and re-centrifuged (5,000 RPM, 10 minutes at 4° C.). The final spore pellet was then resuspended in a 12% skimmed milk suspension (Sigma) in water to a homogeneous suspension and then aseptically dispensed in 0.5 mL aliquots into lyophilization vials. Vials were then frozen and followed by lyophilization, and the lyophilized master seed stock vials were then sealed under vacuum and stored at room temperature or for longer term storage maintained at 5±3° C. in a refrigerator.

6.2. Preparation of a Working Stock

Preparation of a working stock for pilot-scale fermentation manufacturing followed a procedure as generally illustrated in FIG. 5 (lower portion). The contents of a lyophilized master stock vial were aseptically transferred to a KH media-containing tube and suspended by vortexing. The suspended pellet was transferred to flasks containing KH media and glass beads, which are incubated in an orbital shaker for 84±12 hours, as described in section A above. Contents of the culture flasks were subsequently transferred onto GYM agar plates and incubated as described above. Spores when then collected as described above, washed and aseptically transferred to a tube and centrifuged as described above. Following centrifugation, the pellet was resuspended in water, filtered, re-centrifuged and the supernatant removed. The spore pellet was then subsequently resuspended in a 20:80 glycerol:water solution, vortexed and aliquoted in vials as working stocks to be used for generation of pilot-scale fermentation cultures. Working stock aliquots are stored at −70±10° C.

6.3. Preparation of Working Seed Plates

A working stock vial was retrieved from storage and maintained on dry ice. GYM agar plates where thereafter streaked using a bacteriological loop containing a working stock scraped from the vial with the loop. Streaked plates were inverted and incubated for about 15 to about 20 days at 28±1.0° C. to obtain a bacterial lawn with dark, waxy spores on the surface.

6.4. Incubation of the Seed Flasks

Figure 6:
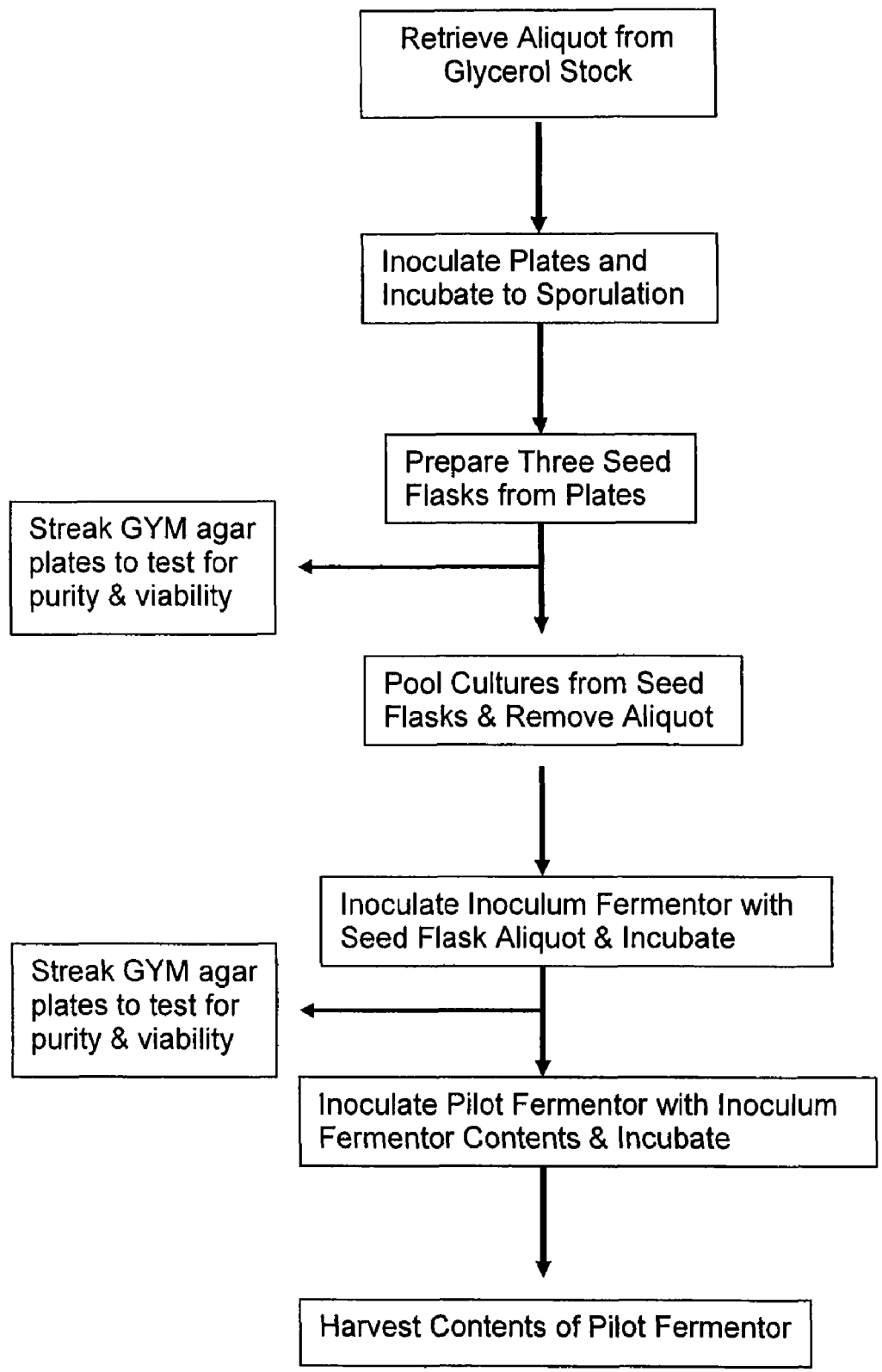
FIG. 6 is a flowchart depicting a plurality of steps involved in a procedure for the preparation production of seed flask fermentations, inoculum fermentations for use with pilot plant fermentations, and a pilot plant fermentation.

Preparation of seed flasks for pilot-scale fermentation manufacturing followed a procedure as generally illustrated in FIG. 6 (upper portion). Surface growth, comprising cell mass and spores, from each GYM agar plate was transferred to three, 2 L baffled flasks containing 500 mL of sterile KH medium per flask, and the inoculated flasks were incubated for 70 to 72 hours at 28±1.0° C. on an orbital shaker operating at about 300 RPM to produce seed cultures. Purity and viability of the seed cultures was verified by in-process testing consisting of microscopic examination of aliquots taken from the growing cultures at about 48 hours and at about 72 hours post-inoculation of the flasks, and also by streaking GYM agar at these point-inoculation timepoints.

6.5. Fermentation of Inoculum Fermentor

Culture material from the three seed flasks was pooled (FIG. 6, lower portion), and under aseptic conditions, a volume (450 mL) of the pooled material equivalent to about 3% of a volume of culture medium present in a 28 L capacity inoculum fermentor (Chemap AG, Type M16K) was transferred aseptically to the inoculum fermentor containing 15 L of KH aqueous culture medium at pH 7. Culture medium was supplemented with 3 mL of Silicone defoamer oil (Chem Service) and 0.75 mL of Proflo oil (Trader Protein; Southern Cotton Oil Co.). Fermentation was performed at 28±1.0° C. for 48±1 hours, with dissolved oxygen maintained at 25% linked to agitation and aeration at 0.55 (V/V/M), and a mixing speed of 110 to 400 RPM. In-process testing assay for purity and viability of the inoculum fermentor culture consisted of microscopic examination and streaking of 24 hour post-inoculation and 48 hour post-inoculation aliquots on GYM agar plates.

6.6. Fermentation in Pilot Fermentor

The entire volume from the inoculum fermentor (FIG. 6, lower portion) was transferred to a 750 L capacity pilot fermentor (Chemap AG, type CF/569) containing 450 L of HI culture medium adjusted to a pH of 7.1. The inoculum volume that was transferred corresponded to about 3.3% of the volume of medium in the pilot fermentor. Silicone defoamer oil (135 mL) and Proflo oil (22.5 mL) were also added to the culture medium before sterilization at 121° C. for 40 minutes. Fermentation was performed at 28±1.0° C. for 95±1 hours, with dissolved oxygen maintained at 25% linked to agitation and aeration at 0.5 to 0.7 (V/V/M), with a mixing speed of the fermentation broth of 80 to 160 RPM, preferably 100 RPM, looped to dissolved oxygen at 25%. In-process controls to test for purity and growth viability consisted of microscopic examination and streaking of fermentation broth aliquots on GYM agar plates at 48, 72 and 96 hour post-inoculation time points.

6.7. Harvesting and Extraction of the Fermentation Broth

Figure 7:
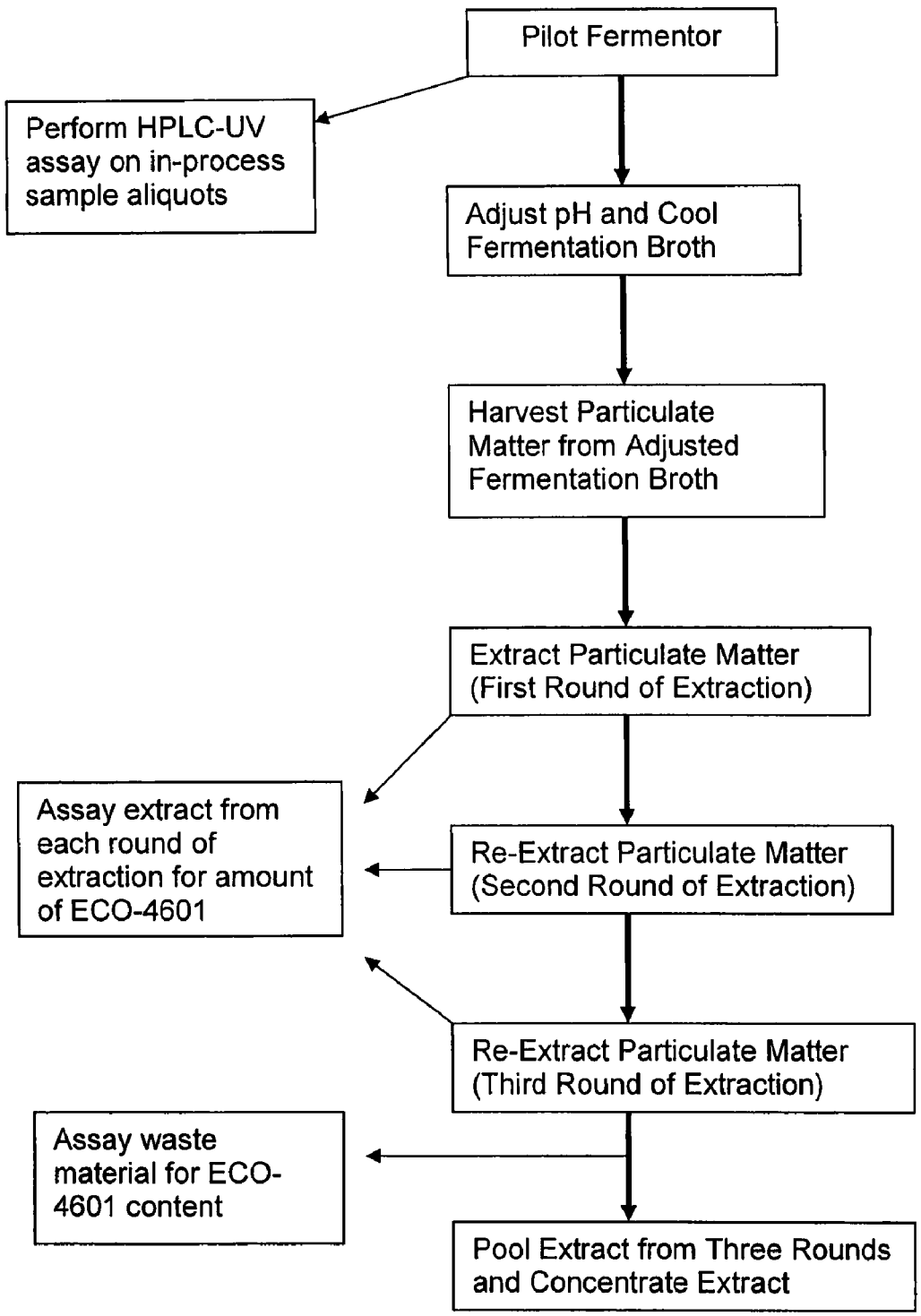
FIG. 7 is a flowchart depicting a plurality of steps for adjustment of a fermentation broth prior to harvesting, harvesting of particulate matter, extracting harvested particulate matter and treating an extract to form a concentrate.

Upon completion of the fermentation (FIG. 7), the pH of the fermentation broth was adjusted in the pilot fermentor to a level of pH 3±0.1 by a slow addition of 99% $H_2SO_4$ with constant stirring. The fermentation broth was then cooled in the pilot fermentor to 14±2° C. and subsequently transferred into a holding tank and held in a refrigeration unit at 4±2° C. for a period of 16 to 72 hours. Upon completion of the cooling period, the cooled fermentation broth was then subjected to ultrafiltration using a 0.2 to 0.45 micrometer pore size filter membrane (filtering time approximately 20 minutes) to produce a thick slurry of harvested mycelia.

To establish values for a concentration and a mass of ECO-4601 in the fermentation broth on completion of the fermentation period, duplicate 0.5 gram aliquots of the separated (filtered) mycelia were placed into separate 50 mL centrifuge tubes. Twenty mL of methanol were then added to each tube, followed by sonification for 5 minutes and vortexing at high speed for 30 seconds. Tubes were then centrifuged at 4000-5000 RPM for 10-15 minutes, and the supernatant from each tube decanted into a clean 50 mL vial. The residual mycelia from each tube were re-extracted, as described above, using 20 mL of methanol. The two methanol extracts per tube were then combined (total volume approximately 40 mL), and a 1 mL aliquot from the combined methanol extract was filtered through a 0.45 um filter membrane. A 10× dilution (in methanol) of the filtered aliquot was then prepared and submitted for quantitative analysis of ECO-4601 by HPLC-UV.

As a qualitative and quantitative check after completion of the filtering of the acidified and cooled fermentation broth, the separated broth supernatant was also assayed for the presence of ECO-4601. Duplicate 5 mL sample aliquots of the broth supernatant were placed in separate 50 mL centrifuge tubes followed by addition of 5 mL ethyl acetate. Tubes were then vortexed at high speed for 1 minute, and centrifuged at 4000-5000 RPM for 10-15 minutes. A 1 mL aliquot from the ethyl acetate layer (upper phase) was withdrawn from each centrifuged tube, placed into a 10 mL glass culture tube and evaporated to dryness under a stream of nitrogen. The dried residue in each tube was re-dissolved in 1 mL of methanol and the resulting solution filtered. The filtrate from each tube was then subjected to HPLC-UV analysis for ECO-4601 content.

ECO-4601 was extracted from the slurry of harvested mycelia by adding 3 L of 100% methanol to every 1 L of the slurry, followed by circulation of the methanol-mycelia slurry mixture at a high velocity (from about 30 Hertz to about 50 Hertz) through an ultrafiltration system for about 60±20 min for an initial extraction round. The high circulating speed was utilized to facilitate the breaking-up of mycelial aggregates, and the temperature was allowed to increase to 42±3° C. during circulation. Optionally, an extended circulation time could be employed, for example 120 minutes, provided however a lower circulation velocity is utilized so as to avoid possible overheating and degradation of the extract. Once the mycelia slurry was properly mixed with the extraction solvent, the valves of the ultrafiltration system were opened to allow the methanol extract to be collected. The methanol extract was fed into a container and the residual mycelia re-extracted with a volume of methanol the same as that used in the first extraction. Residual mycelia from the second round of extraction were re-extracted with a volume of methanol approximately three-eights as that used per the first and second extraction rounds. The circulating time for the third round of extraction was reduced in comparison to the first two rounds of extraction. The three methanolic extracts were pooled and evaporated under reduced pressure using a Buchi Rotavapor® Model R-153 (BUCHI Labortechnik AG, Flawil, Switzerland) to produce a thick, first concentrate.

Quantification of ECO-4601 contained in the methanolic extract per round of extraction was performed as follows. Duplicate 1 mL aliquots of the methanol extract were taken, diluted by 10× with methanol and filtered. The filtered, diluted aliquots were then subjected to HPLC-UV analysis for ECO-4601 content.

As a qualitative and quantitative check after completion of the methanol extraction of the mycelia, extracted waste mycelia (mycelia after the third extraction round) were evaluated for ECO-4601 content. Duplicate 1 gram samples of the extracted waste mycelia were placed into separate 50 mL centrifuge tubes, followed by the addition of 10 mL of ethyl acetate. Tubes were then sonicated for 5 minutes, vortexed at high speed for 30 seconds, and centrifuged at 4000-5000 RPM for 10-15 minutes. A 2 mL aliquot from the ethyl acetate layer (upper phase) was withdrawn from each centrifuged tube, placed into a 10 mL glass culture tube and evaporated to dryness under a stream of nitrogen. The dried residue in each tube was re-dissolved in 1 mL of methanol and the resulting solution filtered. The filtrate from each tube was then subjected to HPLC-UV analysis for ECO-4601 content.

Results from seven separate pilot fermentations are shown below in Table 8.

TABLE 8

Pilot Plant Fermentations

| Pilot-Scale Fermentation Batch No. | Amount of ECO-4601 in Fermentation Broth Upon Harvest | Mass of ECO-4601 in Extract (1st Round) | Mass of ECO-4601 in Extract (2nd Round) | Mass of ECO-4601 in Extract (3rd Round) | Mass of ECO-4601 in Concentrate | Approximate concentration factor ECO-4601 from Broth to 1st Concentrate |
|---|---|---|---|---|---|---|
| PE028 | 78.8 g (175 mg/L) | 54.8 g | 12.2 g | 2.7 g | 69.7 g | 57 |
| PE029 | 76.5 g (170 mg/L) | 43.3 g | 12.7 g | 4.4 g | 60.4 g | 51 |
| PE031 | 67.1 g (149 mg/L) | 37.4 g | 11.2 g | 3.8 g | 52.4 g | 50 |
| PE033 | 66.6 g (148 mg/L) | 46.0 g | 8.4 g | 2.0 g | 56.4 g | 54 |
| PE034 | 57.2 g (127 mg/L) | 33.6 g | 11.3 g | 1.8 g | 46.7 g | 52 |
| PE036 | 65.3 g (145 mg/L) | 42.5 g | 10.7 g | 2.4 g | 55.6 g | 55 |
| PE037 | 65.3 g (147 mg/L) | 42.5 g | 16.0 g | 3.1 g | 61.6 g | 61 |
| PE038 | 76.1 g (169 mg/L) | 49.3 g | 16.3 g | 3.9 g | 69.5 g | 59 |

The average volume of the first concentrate as shown in the last column of Table 8, above, was about 7 L. Results from pilot plant fermentations indicated that on a first round of extraction, the mass of ECO-4601 contained in the methanol extract recovered from the fermentation broth, which could be evaporated to form a concentrate even after the initial round of extraction, ranged between about 55% to about 70% of the amount of ECO-4601 that was calculated to be present in the fermentation broth. On completion of all three rounds of extraction and with the combination of the methanol extracts, the mass of ECO-4601 the present in the first concentrate ranged from about 78% to about 94% of the amount of ECO-4601 that was calculated to be present in the fermentation broth.

Example 7

Increased ECO-4601 Production Using Different Culture Medium 7.1. General Procedure A variety of culture medium were tested for their capability to provide for an elevated level of fermentation production of ECO-4601 relative to a particular preferred culture medium (HI). Small-scale fermentation cultures of *Micromonospora* sp. strain [S01U02]046 were grown under the conditions described above in Example 1 using the individual culture medium as provided in Table 9, noted directly below. Ingredients for each of the culture medium tested are noted in Table 1. For each small-scale fermentation culture, harvesting and extraction of the fermentation broth also followed the procedure as provided in Example 1, as were the HPLC analyses of the extracted broth in order to quantify production of ECO-4601 per each culture medium type used.

7.2. Results

The amount of ECO-4601 produced per culture medium type is expressed as an improvement factor relative to culture medium HI, the improvement factor being calculated as a ratio of an average of the yield per media (mg/L) tested in two separate fermentation culture experiments (two 125 mL flasks per media type per experiment) to the average of the yields in two control cultures grown in HI culture medium. Results from these small-scale fermentation culture experiments are summarized in Table 9.

TABLE 9

Small-scale fermentation cultures using different culture medium

| Culture medium | JA | DZ | YB | GP | AP | PI | QP | QI | CA | MI | HI |
|---|---|---|---|---|---|---|---|---|---|---|---|
| Improvement Factor (relative to HI media) | 4.45 | 4.3 | 3.5 | 3.3 | 3 | 3 | 2.7 | 2.7 | 2.7 | 2.3 | / |
| Standard Deviation (of Improvement Factor | 2 | 0.4 | 1.3 | N/A* | 0 | 0.4 | 0.4 | 0.1 | 0.9 | 0.4 | / |

*Not Available - results are from one experiment.

Example 8

Scale Up Production-Large Volume/Pilot Plant Fermentation

Preparation of pilot manufacturing seeds stocks, working stock, working seed plates, seed flasks, fermentation of inoculum fermentor, and fermentation in pilot fermentor were as described in Example 6.

8.1 Harvesting and Extraction of the Fermentation Broth

Figure 8:
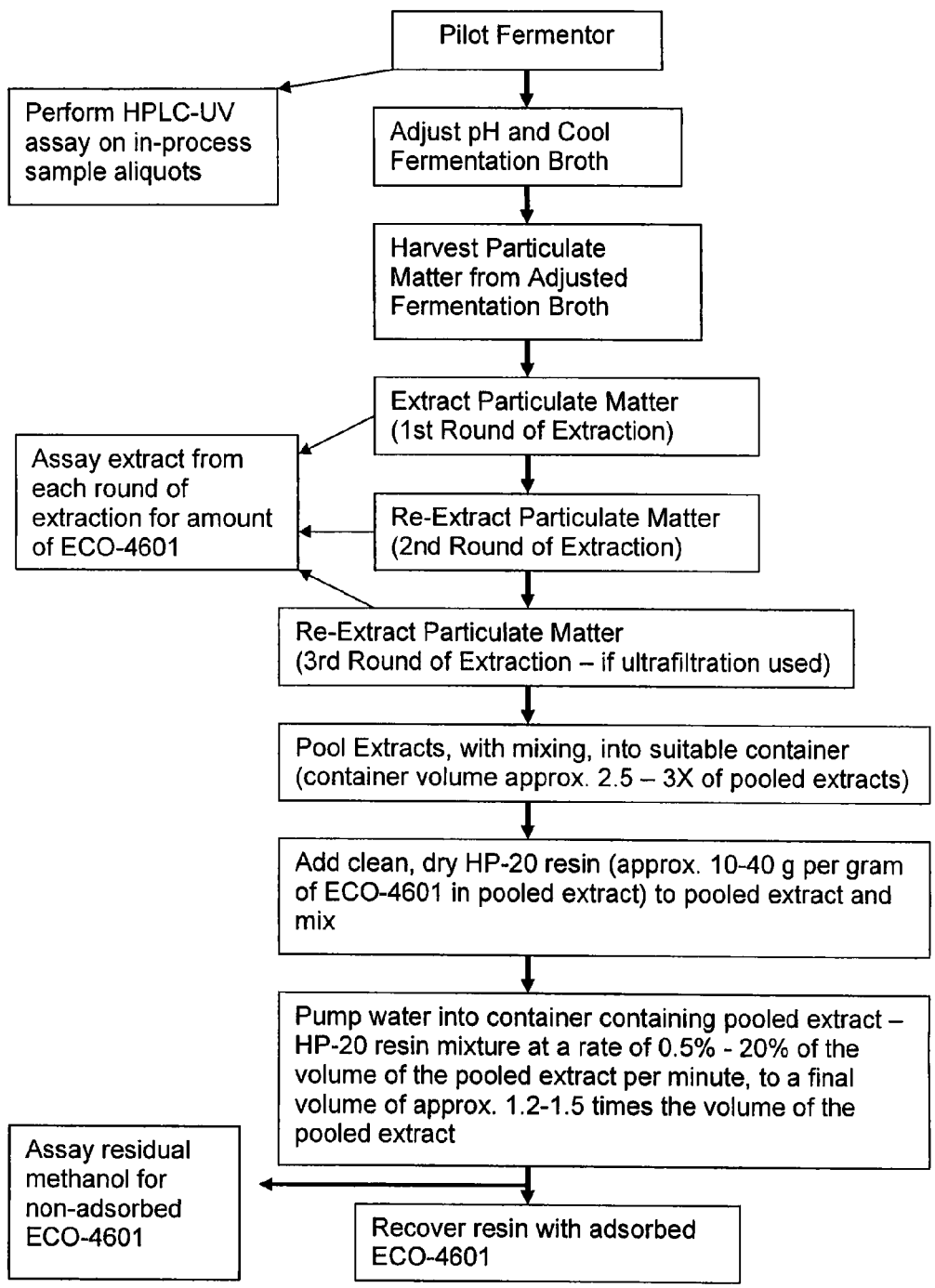
FIG. 8 is a flowchart depicting a plurality of steps involved in a procedure for the displacement of ECO-4601 from pooled extracts onto a resin.

Upon completion of the fermentation, the pH of the fermentation broth was adjusted in the pilot fermentor to a level of pH 3±0.1 by slow addition of 99% $H_2SO_4$ with constant stirring. The fermentation broth was then cooled in the pilot fermentor to 4±2° C. and subsequently transferred into a holding tank and held in a refrigeration unit at 4±2° C. for a period of 16 to 72 hours. Upon completion of the cooling period, the cooled fermentation broth was subjected to either a continuous centrifugation (5,000-20,000 RPM) or batch centrifugation (5,000-20,000 RPM) to produce a paste of mycelia. Calculations of the concentration of the mass of ECO-4601 in the fermentation broth upon completion of the fermentation, and also upon post-collection of the slurry of harvested mycelia, were conducted as described in Example 6, and as also illustrated in FIG. 8. Optionally, upon completion of the cooling period, the cooled fermentation broth may be subjected to ultrafiltration, as per the method described in Example 6, to produce a slurry of harvested mycelia.

8.2 Extraction of the Mycelia Paste

ECO-4601 was extracted from the paste of harvested mycelia with the addition of 8 L (a range of 5 L to 10 L may be used) of 100% methanol to every one kg of mycelial paste followed by mixing for approximately 30 minutes±10 minutes at 250±50 RPM at 25±3° C., followed by circulation of the methanol-mycelia mixture in an filtration system as previously described in Example 6. Following a first round of extraction, the extracted mycelial paste was subjected to a second round of extraction of the residual mycelia using a volume of methanol as per the first round of extraction. Quantification of ECO-4601 contained in the methanolic extract per round of extraction was performed as per Example 6.

8.3 Displacement of Extracted ECO-4601 onto Adsorbent Resin

On completion of the rounds of extraction, the ECO-4601 methanolic extracts from each round were pooled, with mixing, into a stainless steel tank (compatible with organic solvents such as methanol) having a volume of approximately 2.5-3 times the volume of the pooled extract, as illustrated in FIG. 8. Pre-cleaned, dry, HP20 resin was then added to the tank and mixed with the pooled extracts at a speed of 100-300 RPM at room temperature (5° C.-40° C.). The amount of HP20 resin added was calculated on the basis of 10 g of resin for every 1 g of ECO-4601 calculated to be present in the pooled extract, although the amount of resin that can be added can range from about 10 g to about 40 g for every 1 g of ECO-4601 calculated to be present in the pooled extract. Upon completion of the second round of methanol extraction, the extracted mycelia (together with the internal surface of the container and system in which the rounds of extraction were performed) were washed with a further volume of 250 L of methanol to remove a residual amount of ECO-4601 that may have remained on the extracted mycelia or surface. The ECO-4601-bearing wash was thereafter combined with the first and second round extractions to form a pooled methanolic extract.

To displace the ECO-4601 from the pooled ECO-4601 methanolic extracts onto the adsorbent HP20 resin added to the pooled methanolic extract, water (USP-grade) was pumped into the tank (with mixing) at a volumetric rate of about 0.5% to about 20% of the volume of the pooled extracts per minute (i.e. for a 100 L pooled extract, water was pumped into the tank at a rate of abut 0.5 L to about 20 L per minute), and more preferably at a rate of about 0.5% to about 5% of the volume of the pooled extract per minute. A total volume of water pumped into the tank was about 1.2 to about 1.5 times the total volume of the pooled extract. To provide sufficient displacement of the ECO-4601 from the pooled methanolic extracts onto the HP20 resin, the total volume of water to be pumped into the tank may comprise a volume that is about equal to the total volume of the pooled extract. Upon completion of the pumping the total volume of water into the tank containing the pooled ECO-4601 methanolic extracts/HP20 resin mixture, the pooled extract/HP20 resin/water mixture was allowed to incubate at room temperature (5° C.-40° C.) with rotation (100 RPM to 300 RPM) for a period of about 7.5 minutes. Optionally, the mixture may be allowed to incubate for a period of about 5 minutes to about 60 minutes. Upon completion of the incubation period, the HP20 resin bearing the adsorbed ECO-4601 was thereafter recovered by filtration, for example, by using a Hayward bag filter assembly unit; type FBF-0102-AB10 (Hayward, Inc.) equipped with a 50 μm Hayward bag filter membrane (GAF nylon filter, Part #: PO2Z-E-20S), as would be practiced by a person of skill in the art. On completion of the recovery of the ECO-4601 from the resin, the amount of ECO-4601 remaining in the pooled methanol extracts was assayed for by taking duplicate 1 mL aliquots of the methanol extract, followed by HPLC-UV analysis up the filtered diluted aliquots for ECO-4601 content.

8.4 Results

Results from a pilot fermentation wherein ECO-4601 was extracted and displaced onto an adsorbent resin using the water displacement technique as described above are shown below in Table 10.

TABLE 10

| Pilot Plant Fermentation (1000 L) | | | | | |
|---|---|---|---|---|---|
| Amount of ECO-4601 in Fermentation Broth Upon Harvest | Mass of ECO-4601 in Extract (1st Round) | Mass of ECO-4601 in Extract (2nd Round) | Mass of ECO-4601 from wash | Mass of ECO-4601 in Waste Mycelia | Mass of ECO-4601 in Concentrate |
| 125.1 g | 85.3 g | 11.4 g | 25.2 g | 3.2 g | 121.9 g |

Results from the pilot plant fermentation indicated the mass of ECO-4601 recovered from the fermentation broth, as calculated to be present on the extract-bound resin recovered from the pooled methanol extracts upon completion of the displacement step, to be approximately 97.4% of the amount of ECO-4601 that was calculated to be present in the fermentation broth.

Example 9

Downstream Processing of Resin-Adsorbed Farnesylated Dibenzodiazepinone

A first concentrate comprising the resin-absorbed farnesylated dibenzodiazepinone can be subjected a further downstream processing in order to reduce a level of an impurity, such an impurity potentially having a deleterious effect or effects such as upon the crystallization of the ECO-4601. To reduce the level of such an impurity, ECO-4601 that has been displaced onto the adsorbent resin was subjected to rounds of column cleanup, wherein for a first-round cleanup, an HP20 column was prepared by transferring 2.5±0.2 kg of pre-cleaned HP20 in 20% aqueous methanol to a 30 L capacity column and the column thereafter eluted until the HP20 resin was settled in the column so as to form a resin bed in the column. HP20 resin bearing approximately 315 grams of ECO-4601 (colour of the HP20 resin bearing the ECO-4601 was a reddish to brownish/dark brown) was then transferred into the column without disturbing the clean bed of HP20. The HP20 resin bearing the approximately 315 grams of ECO-4601 resulting from the displacement treatment, as described above in Example 8, of extract having 339.2 grams of ECO-4601. Upon completion of the transfer of the HP20 resin bearing the 315 grams of ECO-4601 into the column, the column was then eluted with 150±5 L of 65% aqueous methanol at a flow rate of 400 mL/min and the effluent from the elution with the 65% aqueous methanol was discarded. After the 65% aqueous methanol elution step, the column was then eluted with 150±5 L of 70% aqueous methanol at a flow rate of 400 mL/min and the effluent collected in 20 L fractions. Upon completion of the 70% aqueous elution, the column was thereafter eluted with 100±5 L of 90% aqueous methanol at a flow rate of 400 mL/min and the effluent collected in 20 L fractions. The 20 L fractions from the 70% aqueous methanol and the 90% aqueous methanol elution steps were assayed for the presence of ECO-4601, and fractions having greater than or equal to 1% ECO-4601 were combined so as to form a pool of aqueous methanol fractions containing ECO-4601 from the first-round cleanup. The pool of aqueous methanol fractions containing approximately 304 grams of ECO-4601 was then subjected to a second-round cleanup.

For the second-round cleanup, the pool of aqueous methanol fractions containing the approximately 304 grams of ECO-4601 from the first-round cleanup was transferred into a 350 L mixing tank. Pre-cleaned HP20 resin was then added to the mixing tank in an amount of 18±2 L with rotation of the mixer at 120±10 RPM. Water (UPS-grade) was thereafter pumped into the tank at a volumetric rate of 2±0.5 L/min to a total volume equal to the volume of the pooled methanol fractions from the first-round cleanup. On completion of the pumping of the water into the tank, the HP20 bearing the ECO-4601 was recovered using a bag filter assembly unit and filter as described in Example 8. For the second-round cleanup, an HP20 column was prepared by transferring 2.5±0.2 kg of pre-cleaned HP20 in 5 L of 20% aqueous methanol to a column, after which the column was washed with 20% aqueous methanol and the HP20 resin allowed to settle in the column so as to form a resin bed in the column. After settling of the column was completed, the HP20 resin onto which the ECO-4601 had been displaced was transferred to the column and the column washed with 30% aqueous methanol. Thereafter, the column was eluted with 150±5 L of 65% aqueous methanol at a flow rate of 400 mL/min and the effluent from the elution with the 65% aqueous methanol was discarded. After the 65% aqueous methanol elution step, the column was then eluted with 150±5 L of 70% aqueous methanol at a flow rate of 400 mL/min and the effluent collected in 20 L fractions. Upon completion of the 70% aqueous methanol elution, the column was thereafter eluted with 100±5 L of 90% aqueous methanol at a flow rate of 400 mL/min and the effluent collected in 20 L fractions. The 20 L fractions from the 70% and the 90% aqueous methanol elution steps were assayed for the presence of ECO-4601, and fractions having greater than or equal to 1% ECO-4601 were combined so as to form a pool of aqueous methanol fractions containing ECO-4601 from the second-round cleanup. The pool of aqueous methanol fractions containing approximately 278 grams of ECO-4601, and the pool of aqueous methanol fractions was thereafter evaporated to provide a second concentrate having a grayish to greyish-brown colour. While the level of any particular impurity that may remain in the second concentrate after the processing may vary, the second concentrate is to be considered to be substantially free of molecules other than the farnesylated dibenzodiazepinone of Formula I. From the second concentrate, acrystalline farnesylated dibenzodiazepinone of Formula I may be produced upon subjecting the second concentrate to a crystallization process.

Example 10

Crystallization

A second concentrate may be utilized for the production of crystalline ECO-4601. A 33% ethanol crystallization solution can be prepared in a 500 L crystallization tank, with stirring at 140±20 RPM. The temperature of the crystallization solution is allowed to equilibrate at 30±2° C. for 120±10 minutes. A sample solution for crystallization can be prepared by dissolving the second concentrate (resulting from the two rounds of cleanup processing the HP20 column (as described above in Example 8)) by mixing the second concentrate in absolute ethanol (24±3 g/L). The second concentrate is to be mixed well with the absolute ethanol in order to dissolve the second concentrate into the absolute ethanol, for example, by manual mixing for 7.5±2.5 minutes. Purified water is then added to the ethanolic solution while stirring and the resulting solution filtered through a 0.45 μm to 10 μm membrane filter. The sample solution may then be pumped into the crystallization tank at a rate (mL/min) that is about 10 mg/min/10 L of crystallization solution volume. During the pumping of the crystallization solution, nitrogen gas or purified air is to be flowed over the crystallization tank at a flow rate of 20±2 L/min. The temperature of the tank is to be maintained at 30±2° C. while mixing the sample solution with the 33% ethanolic solution at 40±10 RPM. As the sample solution is being pumped into the crystallization tank, the crystallization tank is to be seeded with 75±25 mg of ECO-4601 in water, and the delivery of the sample solution into the crystallization tank completed. ECO-4601 crystals are to be allowed to mature for 14±2 hours, with nitrogen gas flowing over the crystallization tank at a flow rate of 10±2 L/min and mixing occurring at 40±10 RPM while the tank temperature is maintained at 30±2° C. Purified water is to thereafter be pumped into the crystallization tank at a rate (mL/min) about equal to the volume of water to be added divided by 1200, and the crystals allowed to mature for 24±4 hours with nitrogen gas flowing over the crystallization tank at a flow rate of 10±2 L/min and mixing occurring at 40±10 RPM while the tank temperature is maintained at 30±2° C. At the completion of the maturity period, the mixing is to be stopped and crystals allowed to settle for 18±6 hours. To harvest the settled crystals from the crystallization tank, the supernatant from the crystallization tank is to be drained into a holding tank and the settled crystals (in the form of a slurry) are to be drained into a receiving tank and recovered by filtration through a 10-20 μm scintered glass filter funnel. Recovered crystals are then to be re-suspended in cold (about 4° C.). 10% ethanol and filtered again, with the resuspension and filtering being twice repeated. The crystals are then to be allowed to anneal in a vacuum oven (operating at about at least equal to or greater than a pressure of 25 inches of Hg, 68±2° C.) for 21±5 hours. On completion of the annealing, the annealed crystals (having a needle-like shape) may then be transferred to a container, preferably a polypropylene container, and stored at 25±2° C.

Example 11

Demonstration of a Purification of a Specific Batch Resulting in an Incremental Purity Level of ECO-4601 Relative to the Purity of the ECO-4601 in the Fermentation Broth As an example of a measure of an increase in a purity level of ECO-4601 from a fermentation broth stage to production of crystalline ECO-4601, a pilot scale fermentation broth batch (record number DR00116) (produced in accordance with the procedure described in Example 6) of 450 L (having a mss of about 450 kg) was calculated to contain about 78 grams of ECO-4601. A cell mass of the microorganism producing the farnesylated dibenzodiazepinone of Formula I of about 22.5 kg (comprising about 5% of the mass of the fermentation broth upon completion of the fermentation process) was calculated to be present in the broth. As such, upon completion of the fermentation period, a purity level of about 0.35% of ECO-4601 was calculated to be present in the fermentation broth (78 grams divided by (0.05×450,000 grams). Levels of purity of the ECO-4601 in the fermentation broth upon completion of the fermentation period may be estimated to range from at least about 0.3% to about 1%. Upon subjecting the first concentrate (generated from treatment of the extract of the fermentation broth) to a first round of column cleanup, the calculated purity of the ECO-4601 resulting from such first round of cleanup was about 66%, and upon completion of the second round of column cleanup (as described above in Example 9) the purity of the ECO-4601 comprising the so-formed second concentrate was calculated to be about 88.5%. Thereafter, upon subjecting the second concentrate to the crystallization process, the resultant crystals were calculated to be about 99% ECO-4601.

In case of conflict, the present specification, including definitions, will control. While this invention has been particularly shown and described with reference to the preferred embodiments thereof, it will be understood by those skilled in the art that various changes in form and details may be made without departing from the scope of the invention encompassed by the appended claims.

All documents, publications and other materials cited herein, including but not limited to, patents, patent application publications, journal articles, books, product literature and manuals, are expressly incorporated herein by reference in their entirety.

What is claimed is:

1. A process for recovering and concentrating the farnesylated dibenzodiazepinone of structural Formula I

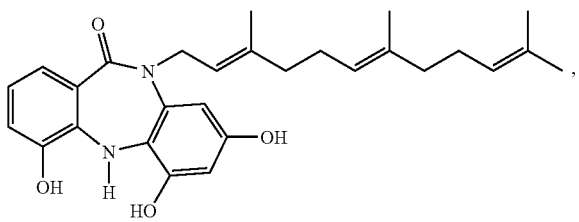

Formula I comprising:
 a) fermenting a strain of a microorganism that produces the farnesylated dibenzodiazepinone of Formula I in an aqueous culture medium, thereby producing a fermentation broth comprising said farnesylated dibenzodiazepinone, wherein the bacterium is *Micromonospora* sp. [S01]046 having IDAC accession number 231203-01 or *Micromonospora* sp. [S01U02]046 having IDAC accession number 070905-01;
 b) adjusting said fermentation broth by acidification to a pH value of between about 2 to 4 to allow said farnesylated dibenzodiazepinone to associate with a particulate matter present in said broth;

c) harvesting said particulate matter from said broth, thereby obtaining a harvested particulate matter;

d) extracting said harvested particulate matter with a volume of an organic solvent in a proportion of about 2:1 to about 5:1 to said harvested particulate matter, thereby forming an extract; and e) subjecting said extract to evaporation or water displacement, thereby forming a first concentrate comprising said farnesylated dibenzodiazepinone of Formula I, wherein said first concentrate comprises said farnesylated dibenzodiazepinone at a concentration greater than about 50-fold than said farnesylated dibenzodiazepinone in said fermentation broth of a), and wherein at least about 50% of the amount of said farnesylated dibenzodiazepinone in said fermentation broth of a) is recovered in said first concentrate.

2. The process of claim 1, wherein the particulate matter comprises the microorganism present in the fermentation broth.

3. The process of claim 2, wherein the particulate matter further comprises a first adsorbent resin.

4. The process of claim 1, wherein the organic solvent comprises i) at least one lower alkyl alcohol selected from the group consisting of ethanol, propanol, iso-propanol, butanol or methanol, or a mixture thereof; ii) ethyl acetate; and iii) acetonitrile.

5. The process of claim 1, wherein the harvesting of (c) is by ultrafiltration or by centrifugation.

6. The process of claim 1, wherein step (d) comprises one to three rounds of extraction using the organic solvent.

7. The process of claim 1, wherein the volume of the organic solvent is calculated in proportion to the harvested particulate matter mass or to the harvested particulate matter volume.

8. The process of claim 1, wherein the extract is subjected to evaporation.

9. The process of claim 1, wherein the subjecting step (e) is water displacement, wherein said water displacement comprises incubating the extract with an absorbent resin to form a mixture, followed by an addition of water to the mixture to displace the farnesylated dibenzodiazepinone of Formula I onto the resin added at step (e), thereby forming the first concentrate comprising the farnesylated dibenzodiazepinone.

10. The process of claim 1, wherein said fermentation broth of a) comprises about 10 mg/L to about 465 mg/L of said farnesylated dibenzodiazepinone.

11. The process of claim 1, further comprising processing said first concentrate obtained by the method of claim 1 to reduce a level of an impurity in said first concentrate to thereby produce a second concentrate.

12. The process of claim 11, further comprising the step of crystallizing from said second concentrate the farnesylated dibenzodiazepinone of Formula I to thereby produce a crystal of the farnesylated dibenzodiazepinone of Formula I suitable for use in the preparation of a pharmaceutical formulation.

13. The process of claim 9, wherein the adsorbent resin added at step (e) is mixed with the extract in a ratio (W/W) of about 10 times to about 40 times of the farnesylated dibenzodiazepinone of Formula I present in said extract, and wherein the water is added to the mixture at a volumetric rate (V/V) of about 0.5% to about 20% per minute of the volume of the mixture.

* * * * *